(12) United States Patent
Hayashi et al.

(10) Patent No.: US 10,475,711 B2
(45) Date of Patent: Nov. 12, 2019

(54) METHOD FOR EVALUATING QUALITY OF OXIDE SEMICONDUCTOR THIN FILM, METHOD FOR MANAGING QUALITY OF OXIDE SEMICONDUCTOR THIN FILM, AND DEVICE FOR MANUFACTURING SEMICONDUCTOR USING SAID METHOD FOR MANAGING QUALITY

(71) Applicant: KOBE STEEL, LTD., Hyogo (JP)

(72) Inventors: Kazushi Hayashi, Hyogo (JP); Mototaka Ochi, Hyogo (JP); Toshihiro Kugimiya, Hyogo (JP)

(73) Assignee: Kobe Steel, Ltd., Hyogo (JP)

( * ) Notice: Subject to any disclaimer, the term of this patent is extended or adjusted under 35 U.S.C. 154(b) by 0 days.

(21) Appl. No.: 16/096,093

(22) PCT Filed: Apr. 26, 2017

(86) PCT No.: PCT/JP2017/016576
§ 371 (c)(1),
(2) Date: Oct. 24, 2018

(87) PCT Pub. No.: WO2017/188323
PCT Pub. Date: Nov. 2, 2017

(65) Prior Publication Data
US 2019/0122941 A1    Apr. 25, 2019

(30) Foreign Application Priority Data
Apr. 27, 2016  (JP) .................................. 2016-088984

(51) Int. Cl.
*H01L 21/66*    (2006.01)
*G01N 22/02*    (2006.01)
*H01L 21/02*    (2006.01)
*H01L 29/24*    (2006.01)
(Continued)

(52) U.S. Cl.
CPC ............. *H01L 22/12* (2013.01); *G01N 22/02* (2013.01); *H01L 21/02565* (2013.01);
(Continued)

(58) Field of Classification Search
CPC ............... H01L 22/12; H01L 21/02631; H01L 29/7869; H01L 29/24; H01L 29/32; H01L 21/02565; G01N 22/02
See application file for complete search history.

(56) References Cited

U.S. PATENT DOCUMENTS

2015/0355095 A1    12/2015  Hayashi et al.
2015/0371906 A1    12/2015  Kishi et al.
(Continued)

FOREIGN PATENT DOCUMENTS

JP     2015-130404 A     7/2015
TW      201428266 A      7/2014
(Continued)

OTHER PUBLICATIONS

Aya Hino et al.; "Effect of H and OH desorption and diffusion on electronic structure in amorphous In—Ga—Zn—O metal-oxide-semiconductor diodes with various gate insulators"; Journal of Applied Physics; 2012; pp. 114515-1 to 114515-7; vol. 112, 114515; American Institute of Physics.
(Continued)

*Primary Examiner* — Michael Jung
(74) *Attorney, Agent, or Firm* — Studebaker & Brackett PC

(57) ABSTRACT

A quality evaluation method for an oxide semiconductor thin film includes: selecting a peak value having a largest calculated value and a time constant for the peak value among calculated values obtained by substituting each signal value for respective elapsed times after stopping excitation light irradiation and the corresponding elapsed time into the
(Continued)

following Equation (1); and estimating, from the peak value and the time constant, an energy level of defect state and the defect density in the oxide semiconductor thin film:

$$x = \text{(signal value)} \times \text{(elapsed time for the signal value)} \qquad \text{Equation 1.}$$

9 Claims, 10 Drawing Sheets

(51) Int. Cl.
  *H01L 29/32* (2006.01)
  *H01L 29/786* (2006.01)
(52) U.S. Cl.
  CPC ........ *H01L 21/02631* (2013.01); *H01L 29/24* (2013.01); *H01L 29/32* (2013.01); *H01L 29/7869* (2013.01)

(56) References Cited

U.S. PATENT DOCUMENTS

| | | |
|---|---|---|
| 2016/0197198 A1 | 7/2016 | Takeda et al. |
| 2016/0223462 A1* | 8/2016 | Hayashi ............. G01N 21/6489 |
| 2016/0282284 A1* | 9/2016 | Hayashi ................. G01N 22/00 |
| 2017/0184660 A1 | 6/2017 | Hayashi et al. |
| 2017/0194218 A1 | 7/2017 | Kawakami et al. |

FOREIGN PATENT DOCUMENTS

| | | |
|---|---|---|
| TW | 201613006 A | 4/2016 |
| TW | 201614737 A | 4/2016 |
| WO | 2015/033499 A1 | 3/2015 |
| WO | WO-2015083666 A1 * | 6/2015 ............. G01N 22/00 |

OTHER PUBLICATIONS

Jiajun Luo et al.; "Transient photoresponse in amorphous In—Ga—Zn—O thin films under stretched exponential analysis"; Journal of Applied Physics; 2013; pp. 153709-1 to 153709-8; vol. 113, 153709; American Institute of Physics.

International Search Report issued in PCT/JP2017/016576; dated Jul. 25, 2017.

* cited by examiner

US 10,475,711 B2

METHOD FOR EVALUATING QUALITY OF OXIDE SEMICONDUCTOR THIN FILM, METHOD FOR MANAGING QUALITY OF OXIDE SEMICONDUCTOR THIN FILM, AND DEVICE FOR MANUFACTURING SEMICONDUCTOR USING SAID METHOD FOR MANAGING QUALITY

TECHNICAL FIELD

The present invention relates to a method for evaluating the quality of an oxide semiconductor thin film suitable for use in thin film transistors (TFTs) for use in display devices such as liquid-crystal displays and organic EL displays, a method for controlling the quality of said oxide semiconductor thin film, and a semiconductor production apparatus which employs said quality evaluation method.

BACKGROUND ART

Flat panel displays (hereinafter referred to as "FPDs") are required to accommodate higher definition, higher display frequencies, and reductions in power consumption, as a result of the spread of TVs and smartphones. With this trend, the TFTs for use in circuits which drive such displays have come to be required to have high-speed responsiveness, i.e., high mobility as semiconductor characteristics.

Amorphous oxide semiconductor thin films (hereinafter referred to as "oxide semiconductor thin films") are receiving attention nowadays as a semiconductor thin-film material for constituting TFTs. In particular. In—Ga—Zn—$O_4$ (hereinafter referred to as "IGZO") is being investigated as a promising material. IGZO has higher mobility than amorphous silicon (hereinafter referred to as "a-Si"), which has hitherto been used, and is capable of accommodating higher definition and effective in reducing leakage current, and hence has advantages of contributing to a reduction in the power consumption of FPDs. IGZO is consequently expected to be used in applications such as next-generation displays, which are required to have a larger size and higher resolution and to be driven at a higher speed.

However, there are cases where an oxide semiconductor thin film has electrical defects introduced therein due to a compositional change attributable to the inclusion of multiple components, a structural fluctuation attributable to the amorphousness, etc. An oxide semiconductor thin film, in particular, considerably changes in carrier concentration, which governs the TFT characteristics, because of lattice defects generated in the deposition step or of hydrogen in the film, or changes in electronic state because of a subsequent heat treatment, thereby affecting the quality of the TFT. Thus, there are fluctuations in mobility due to film quality and the threshold voltage ($V_{th}$) shifts through imposition of negative-bias stress under light irradiation result in changes in switching characteristics, etc., and there is a problem in that these affect the TFT characteristics. For example, a TFT employing IGZO which has been incorporated into an FPD deteriorates in switching characteristics because of stress due to light to which the TFT is exposed during use or due to a voltage applied thereto during standby. Meanwhile, in FPDs employing OLEDs (organic light emitting diodes), the $V_{th}$ shifts due to the influence of a positive-direction driving voltage for causing the OLEDs to luminesce. Since the TFT characteristics are attributable to the electronic state of the oxide semiconductor thin film, it is considered that the deterioration in switching characteristics due to stress is also attributable to a change in the electronic state of the oxide semiconductor thin film.

It is therefore important from the standpoint of improving production efficiency that in steps for producing an oxide semiconductor thin film, the electronic state of the oxide semiconductor thin film should be grasped to evaluate the production process for any influence on the electronic state and the results of the evaluation should be fed back to regulate the production conditions and control the quality of the TFT.

As a method for determining threshold voltage change $\Delta V_{th}$ (hereinafter often referred to as "threshold shift $\Delta V_{th}$"), which affects switching characteristics, an LNBTS (light negative bias temperature stress) test is adopted, which is an accelerated test for simulating the state of a standby TFT which is receiving a negative gate voltage (negative bias) and is continuously irradiated with stray light from a backlight. Meanwhile, a PBTS (positive bias temperature stress) test is adopted as an accelerated test for simulating the state of a standby TFT to which a positive gate voltage (positive bias) is being applied. The LNBTS test and the PBTS test are for determining a change in threshold voltage through stress imposition. The smaller the threshold shift $\Delta V_{th}$, which is calculated from the results of the test, the better the stress stability and the better the practical switching characteristics. Although the LNBTS test and the PBTS test are commonly used as highly reliable evaluation methods, it is necessary, for carrying out these tests, to actually produce a TFT to which electrodes have been attached and this production requires time and cost. There has hence been a desire for a technique capable of more easily and accurately evaluating stress stability.

Patent Document 1 and Non-Patent Document 1 each disclose a method for qualitatively or quantitatively evaluating the stress stability of an oxide semiconductor thin film by a microwave photoconductivity decay method (µ-PCD technique), as a method for evaluating the stress stability of an oxide semiconductor thin film in a non-contact manner without attaching electrodes thereto.

PRIOR ART DOCUMENTS

Patent Document

Patent Document 1: JP-A-2015-130404

Non-Patent Document

Non-Patent Document 1: Journal of Applied Physics, Vol. 112, 053715 (2012)

SUMMARY OF THE INVENTION

Problems that the Invention is to Solve

Patent Document 1 discloses that an oxide semiconductor thin film is measured and evaluated for electronic state between any two of steps for producing a thin film transistor, thereby grasping any defects present in the oxide semiconductor thin film to render quality control of the oxide semiconductor thin film possible. In the technique of Patent Document 1, a threshold shift $\Delta V_{th}$ is estimated on the basis of a slow-decay lifetime of about 1 µsec to evaluate the TFT characteristics. However, it is impossible to sufficiently estimate a threshold shift $\Delta V_{th}$ attributable to defects existing in a longer slow-decay lifetime. Meanwhile, the technique disclosed in Non-Patent Document 1 is for evaluating the activation energy of a defect level from temperature changes. However, since it is necessary to make measurements at a plurality of temperatures, sample alteration is prone to occur at high temperatures. In addition, although activation energy, i.e., energy level, can be grasped, the disclosed technique cannot be used for evaluating defect density.

The present invention has been achieved in view of the circumstances described above. An object of the present invention is to provide a method for accurately and easily evaluating the stress stability of an oxide semiconductor thin film by estimating the energy level of defect existing in the bandgap of the oxide semiconductor thin film and the defect density. Another object is to provide a method for controlling the quality of an oxide semiconductor thin film on the basis of the evaluation and an apparatus for producing a semiconductor.

Means for Solving the Problems

The present invention provides a quality evaluation method with which the problems described above can be overcome, the method including: a first step, which includes irradiating a sample having an oxide semiconductor thin film formed thereover with excitation light and microwave to measure a maximum value of reflectance of the microwave from the oxide semiconductor thin film, subsequently stopping the irradiation with the excitation light, measuring temporal reflectance of the microwave from the oxide semiconductor thin film with the lapse of time after the stopping of the excitation light irradiation, and recording the reflectance of the microwave, as a signal value, for each of elapsed times (μsec) after the stopping of the excitation light irradiation; and a second step, which includes selecting a peak value (N value) having a largest calculated value and a time constant (μsec) for the peak value among calculated values obtained by substituting each signal value for respective elapsed times after stopping the excitation light irradiation and the corresponding elapsed time into the following Equation (1), and estimating, from the peak value and the time constant, an energy level of defect state and the defect density existing in the oxide semiconductor thin film:

$$x = (\text{signal value}) \lambda (\text{elapsed time for the signal value}) \quad \text{Equation 1,}$$

wherein
x: the calculated value,
signal value (mV): the reflectance of the microwave, and
elapsed time for the signal value: the time (μsec) which has elapsed from the stopping of the excitation light irradiation to the signal value).

In a preferred embodiment of the second step, on the basis of a microwave-reflectance elapse curve obtained from the calculated values as ordinate and the time constants (μsec) as abscissa, a peak value (N value) having a largest calculated value and a time constant (μsec) for the peak value are selected.

According to the present invention, on the basis of the peak value (N value) and the time constant for the peak value, light irradiation and negative-bias or positive-bias are applied to a thin film transistor to evaluate threshold voltage change $\Delta V_{th}$ between before and after the application.

In another preferred embodiment of the second step, in the case where a microwave reflectance elapse curve is obtained from the calculated vales as ordinate and logarithms of the time constants (μsec), which are elapsed times after the stopping of the excitation light irradiation, as abscissa, and where the axis of the ordinate and the axis of the abscissa are taken as y-axis and x-axis respectively, a total defect density existing in the oxide semiconductor thin film is estimated from a value of an area surrounded by the elapse curve, the straight line of y=0, a straight line of x=$t_1$, and a straight line of x=$t_2$, wherein $t_1$ and $t_2$ are any time constants satisfying $t_1 < t_2$.

According to the present invention, on the basis of the value of the area surrounded by the elapse curve, the straight line of y=0, the straight line of x=$t_1$, and the straight line of x=$t_2$, light irradiation and negative-bias or positive-bias are applied to a thin film transistor to evaluate threshold voltage change $\Delta V_{th}$ between before and after the application In a desirable embodiment of the present invention, the oxide semiconductor thin film contains at least one element selected from the group consisting of In, Ga, Zn, and Sn.

In a preferred embodiment of the present invention, the oxide semiconductor thin film is deposited on a surface of a gate insulating film or has a passivation film formed on the surface thereof. The present invention includes a method for controlling the quality of an oxide semiconductor thin film using the evaluation method.

The present invention further involves a semiconductor production apparatus which employs the quality evaluation method.

Effects of the Invention

According to the present invention, the stress stability of an oxide semiconductor thin film can be accurately and easily evaluated by estimating the energy level of defects existing in the oxide semiconductor thin film and the defect density. Furthermore, by adopting the evaluation method of the invention in a semiconductor production apparatus, specifically, in steps for producing an oxide semiconductor thin film, the quality of the oxide semiconductor thin film can be appropriately controlled in producing a TFT. The term "stress stability" in the invention means threshold voltage change $\Delta V_{th}$ between before and after light irradiation and negative-bias or positive-bias application to the thin film transistor.

MODE FOR CARRYING OUT THE INVENTION

Mode for carrying out the invention is explained below in detail. The present invention is not limited to the following embodiments.

First Embodiment

A first embodiment of the present invention is explained first. Investigations made so far by the present inventors have revealed that there is the following relationship between the evaluation of an oxide semiconductor thin film by the μ-PCD technique and the stress stability of the TFT.

In the μ-PCD technique, an oxide semiconductor thin film is first irradiated with laser light (hereinafter often referred to as "excitation light") having an energy exceeding a bandgap to generate electron/hole pairs, thereby yielding excess carriers. Although the excess carriers disappear through recombination, the time period to the disappearance (hereinafter referred to as "lifetime") is affected by physical properties of the oxide semiconductor thin film (hereinafter often referred to as "film quality"), such as defect state and density. Furthermore, since the excess carriers which have been generated by the laser light irradiation heighten the electrical conductivity of the oxide semiconductor thin film, the reflectance of microwave changes in proportion to the density of excess carriers. Consequently, in the μ-PCD technique, the lifetime can be determined from changes with time of the reflectance of microwave.

Figure 1:
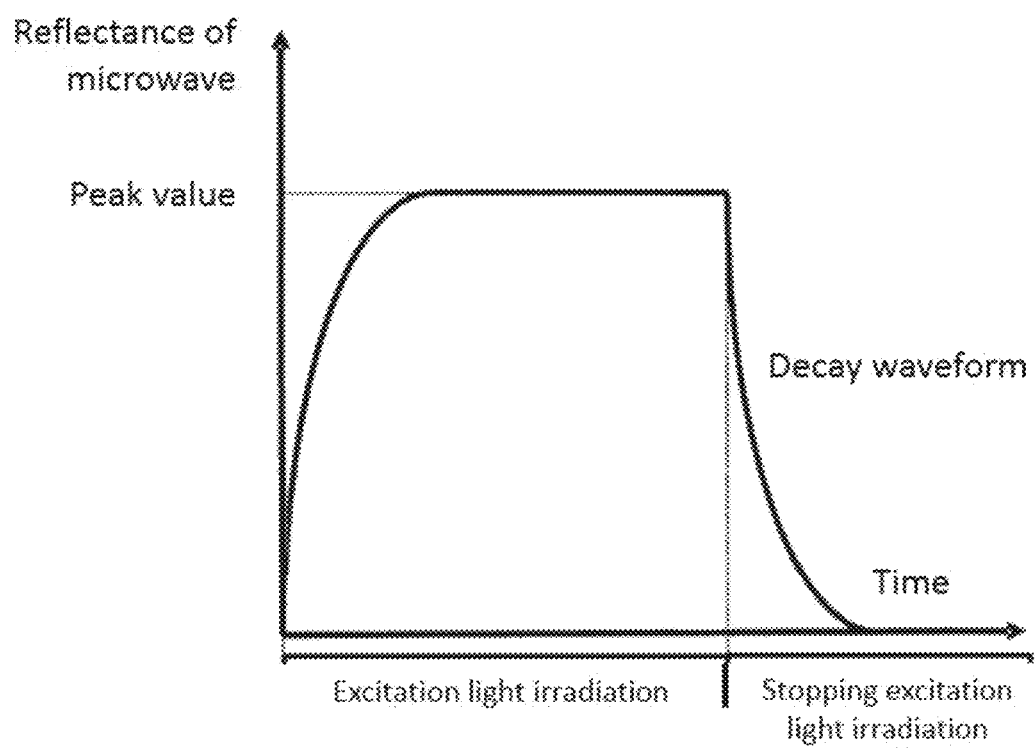
FIG. 1 is a presentation showing a microwave decay waveform.

The microwave decay curve obtained by the μ-PCD technique has such a decay waveform as shown in FIG. 1. The density of excess carriers forms a certain peak when the rate of carrier injection by excitation light irradiation is equal to the rate of carrier disappearance, as shown in FIG. 1. Upon the subsequent stopping of the excitation light irradiation, the excess carriers disappear through recombination, resulting in a decay. Of the decay waveform, decay ranging from the stopping of the excitation light irradiation to 1 μsec therefrom is referred to as fast decay, and decay after the 1 μsec is referred to as slow decay. Patent Document 1 indicates that the slope $\tau_2$ corresponding to about 1 μsec after the stopping of the excitation light irradiation, i.e., $\tau_2$ which is the reciprocal of the slope obtained from a reflected-wave intensity decay curve ranging in reflected-microwave intensity from 1/e to $1/e^2$ the maximum value by subjecting the decay curve to conversion into logarithm, is proportional to the threshold shift $\Delta V_{th}$ and thus correlates thereto.

Figure 5:
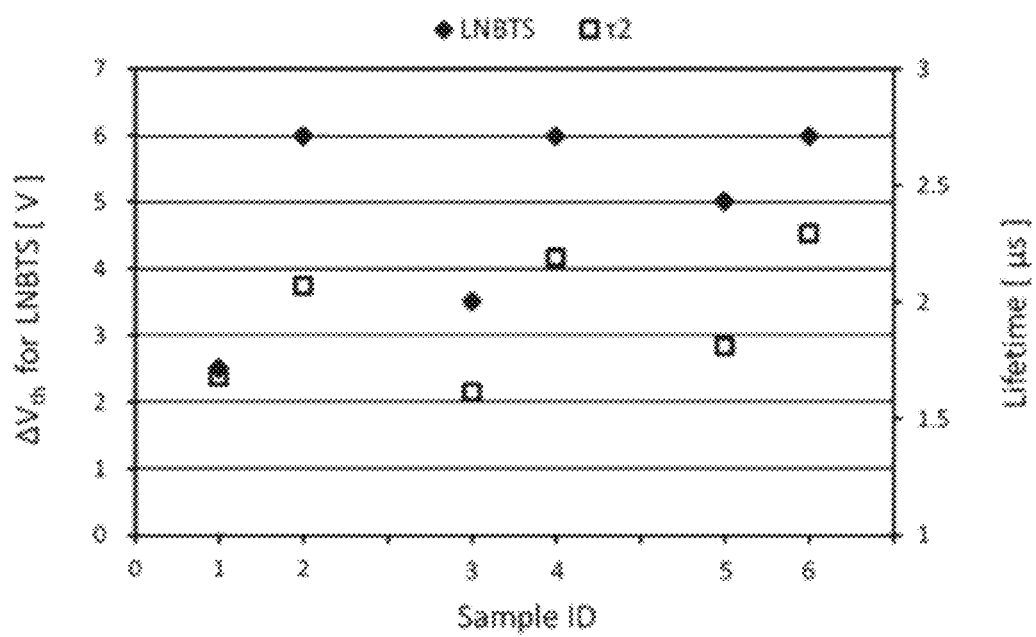
FIG. 5 is a presentation showing a correlation between the LNBTS test and the evaluation method disclosed in Patent Document 1.

However, this evaluation method is nothing but a method for estimating the slope of slow decay, which is attributable to the trap state existing in about 1 μsec after the stopping of the excitation light irradiation, and is unable to evaluate the threshold shift $\Delta V_{th}$ attributable to defects existing in a longer lifetime. For example, as FIG. 5 shows, the lifetime obtained by the evaluation method of Patent Document 1 (slope $\tau_2$ of slow decay acquired from the decay waveform by the μ-PCD technique) and the threshold shift $\Delta V_{th}$ determined through an LNBTS test approximately coincided with each other with respect to Sample No. 3-1, as indicated by Sample ID. 1, but were separated from each other with respect to Sample No. 3-6, as indicated by Sample ID. 6; these results will be described in detail in the Examples. Thus, the method of Patent Document 1 is able to estimate, with high accuracy, the threshold shift $\Delta V_{th}$ for the case where defects exist in a lifetime of about 1-2 μsec, but is unable to sufficiently estimate the threshold shift $\Delta V_{th}$ for the case where defects exist in a later lifetime.

As a result of investigations diligently made by the present inventors, it has been discovered that threshold shift $\Delta V_{th}$ attributable to defects existing in a lifetime later than 1 μsec, for example, in a lifetime from 10 μsec to several tens of microseconds, can be evaluated using the microwave decay waveform.

In the present invention, the first step is conducted to determine a lifetime by the same method as in Patent Document 1. The first step includes: irradiating a sample having an oxide semiconductor thin film formed thereover with excitation light and microwave to measure a maximum value, i.e., a peak, of reflectance of the microwave from the oxide semiconductor thin film and which are changed by the irradiation with the excitation light, subsequently stopping the irradiation with the excitation light, measuring temporal reflectance of the microwave from the oxide semiconductor thin film with the lapse of time after the stopping of the excitation light irradiation, and recording the reflectance of the microwave, as a signal value, for each of elapsed times (μsec) after the stopping of the excitation light irradiation.

Plotting the signal values on a graph as will be described later gives the microwave reflectance decay curve used in Patent Document 1. In the present invention, the elapsed times (μsec) and the signal values for the respective elapsed times are used to conduct the following second step.

Each signal value for the respective elapsed times after the stopping of the excitation light irradiation and the corresponding elapsed time are substituted into the following Equation (1), thereby obtaining calculated values.

$$x = (\text{signal value}) \times (\text{elapsed time for the signal value}) \quad \text{Equation 1}$$

In the Equation, x is the calculated value,
signal value (mV) is the reflectance of the microwave, and
elapsed time for the signal value is the time (μsec) which has elapsed from the stopping of the excitation light irradiation to the signal value.

Next, a peak value (N value) having a largest calculated value and an elapsed time (μsec) corresponding to the peak value are selected among calculated values obtained by substituting each value into the Equation (1). It was found that said peak value corresponds to a relative value of the defect density and the elapsed time (μsec) corresponding to the peak value corresponds to a time constant (μsec) for the defect, i.e., the energy level of the defect.

The reason why the energy level of defect and the defect density can be estimated on the basis of the peak value is considered to be as follows. Electrons trapped by defects existing in the oxide semiconductor thin film are re-emitted into a conduction band in accordance with the time constant calculated using the following Equation (2) and with the energy level thereof.

$$1/\tau = N_e \sigma_n v_{th} \cdot \exp(-\Delta E/kT) \quad \text{Equation (2)}$$

In the Equation,
τ: time constant
$N_e$: effective density of states in the conduction band minimum (CBM)
$\sigma_n$: capture cross section of electron
$v_{th}$: thermal velocity
ΔE: energy change
k: Boltzmann constant
T: absolute temperature The reciprocal of the time constant t is the electron emission rate $e_n$ and corresponds to the number of electrons emitted per unit time period. The change in the number of electrons emitted per unit volume into a conduction band is hence represented by the following Equation (3).

$$dn/dt = N_T \times e_n = N_T \times 1/\tau \quad \text{Equation (3)}$$

In the equation, $N_T$ is the density of defect state which has trapped electrons and has a certain time constant.

By multiplying both sides of Equation (3) by elementary charge, an equation indicating a charge change with the lapse of time, i.e., current, is obtained. Consequently, changes in the reflectance by the μ-PCD technique are equal to changes in photoelectric current attributable to electron emission from trapped electrons. Therefore, by multiplying the signal value for each measuring time in the obtained microwave decay waveform by the measuring time and plotting the product of the microwave reflectance and the time constant as ordinate and each time constant as abscissa, the energy level of defect existing in the oxide semiconductor thin film and the defect density can be relatively evaluated.

It has further been found that the calculated value obtained with Equation (1) and the threshold shift $\Delta V_{th}$ determined by an LNBTS test highly correlate with each other. Although details will be given in the Examples, the evaluation method of Patent Document 1 gave results in which $\tau_2$ was separated from threshold shift $\Delta V_{th}$, as indicated by Sample ID. 6 in FIG. 5, and high-accuracy estimation has been difficult therewith. Meanwhile, the peak value and the threshold shift $\Delta V_{th}$ obtained by the evaluation method of the present invention approximately coincided with each other as indicated by Sample ID. 6 in FIG. 4. With respect to Sample ID. 1 also, the evaluation method of the present invention gave results in which the peak value likewise coincided with the threshold shift $\Delta V_{th}$. Consequently, the evaluation method of the present invention is effective in more accurately estimating threshold shift $\Delta V_{th}$ than the conventional evaluation method. The evaluation method of the present invention is capable of evaluating stress stability by examining reflected microwave in the range of from preferably 0.1 μsec or more, more preferably 0.5 μsec or more, even more preferably 1 μsec or more, most preferably 10 μsec or more, to preferably 100 μsec or less, more preferably 50 μsec or less, even more preferably 30 μsec or less, most preferably 20 μsec or less.

The evaluation method of the present invention is explained below. Examples of devices usable in the present invention include known lifetime measuring devices used in Patent Document 1, etc. The devices are described in detail in Patent Document 1 and JP-A-2012-33857, and reference may be made thereto. However, devices usable in the invention are not limited to those devices.

First, a sample on which an oxide semiconductor thin film has been formed is prepared. Preferred as the oxide semiconductor thin film is a thin film of an amorphous oxide semiconductor containing at least one element selected from the group consisting of In, Ga, Zn, and Sn. Only one of these elements may be contained, or two or more thereof may be used in combination. Specific examples include an In oxide, an In—Sn oxide, an In—Zn oxide, an In—Sn—Zn oxide, an In—Ga oxide, a Zn—Ga oxide, an In—Ga—Zn oxide, and a Zn oxide.

A thickness of the oxide semiconductor thin film is, for example, preferably from several tens of nanometers to about 500 nm. An upper limit of the thickness thereof is more preferably 200 nm or less, even more preferably 100 nm or less. A lower limit of the thickness thereof is more preferably 10 nm or larger, even more preferably 30 nm or larger.

The sample to be used in the invention is one obtained by forming the oxide semiconductor thin film on a substrate. As the substrate, use can be made of various substrates in common use in the field to which the present invention belongs. For example, use can be made of a glass substrate for liquid-crystal display devices which has a thickness of about 0.7 mm and a size (area) of from several tens of square centimeters to larger than several square meters, which is called the first generation to the tenth generation.

This sample is irradiated with excitation light and microwave as stated above. The first step is conducted to measure temporal reflectance of the microwave with the lapse of time, and the reflectance of the microwave for each of elapsed times (μsec) after the stopping of the excitation light irradiation is recorded as a signal value. Each of the elapsed times (μsec) and the signal value for the elapsed time are substituted into Equation (1) to obtain calculated values for the respective elapsed times. For example, the signal values corresponding to elapsed times t1, t2, t3, . . . tz (z is elapsed time) are substituted into Equation (1) to obtain calculated values xt1, xt2, xt3, . . . xtz. A peak value (N value) is selected from among these calculated values, and the elapsed time (μsec) corresponding to the peak value is selected. For the selection, an arithmetic processing means such as a computer may be used. The peak value corresponds to a relative value of the defect density and the elapsed time (μsec) corresponding to the peak value means a time constant (μsec) for the defect and corresponds to the energy level of the defect.

As a method for selecting the peak value and the time constant, use can be made, for example, of a method in which the calculated values and the time constants (μsec) are plotted as ordinate and abscissa, respectively, to obtain a microwave reflectance elapse curve, and a peak value having a largest calculated value and a time constant (μsec) for the peak value are selected on the basis of the elapse curve.

Figure 2:
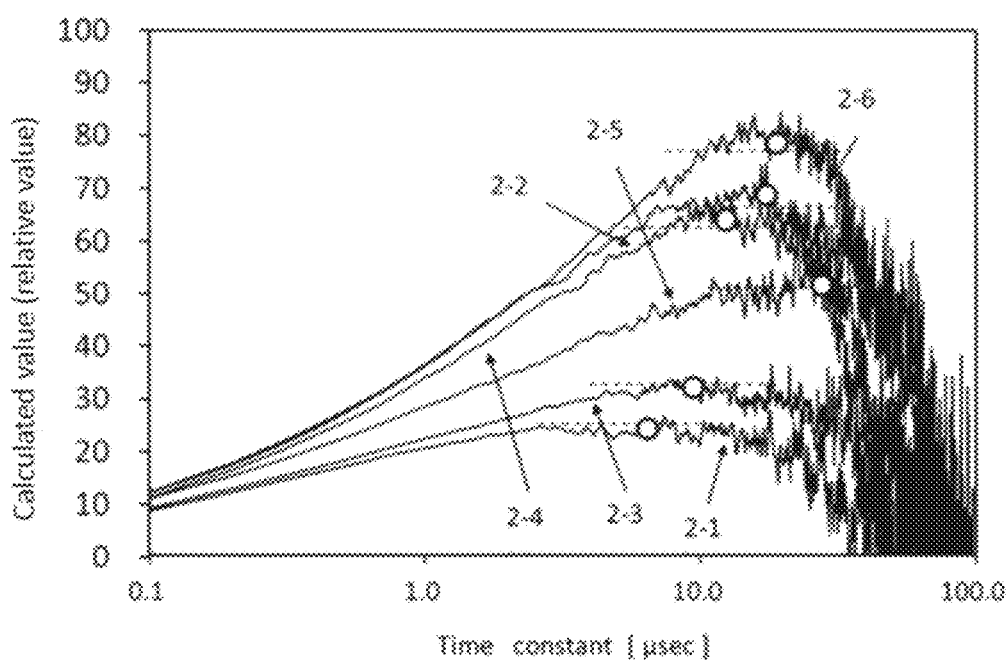
FIG. 2 is graphs obtained by plotting the results obtained in Example 1 (ESL type TFTs) by subjecting reflected-microwave decay waveforms obtained by the μ-PCD technique to the arithmetic processing according to the present invention.

As shown in, for example, FIG. 2, the plot is a curve which forms a peak and then declines. Since a decay curve indicates a defect energy distribution in the conduction band, the curve usually indicates that major defects, e.g., defects which govern the stress properties, have been distributed more extensively than the other defects.

On the elapse curve, a peak value (N value), which is a calculated value located at the highest peak, is specified. From the peak calculated value, the defect density having the time constant can be estimated. From the time constant for the peak value, the energy level of the defect can be estimated. The larger the peak calculated value, the higher the defect density; and the larger the time constant, the deeper the energy level of the defect. Consequently, according to the evaluation method of the invention, the position of defect in the oxide semiconductor thin film and the defect density can be estimated. As described above, the peak value can be used to evaluate the stress stability, specifically, the same threshold shift $\Delta V_{th}$ as in the LNBTS test.

A method for evaluating an oxide semiconductor thin film according to the first embodiment of the present invention was described above.

Second Embodiment

A second embodiment of the invention is explained next. The calculated value obtained by substituting each signal value for respective elapsed times after the stopping of the excitation light irradiation and the corresponding elapsed time into Equation (1), as explained above, corresponds to the density of defect state having a certain time constant and having trapped electrons. In cases where a microwave reflectance elapse curve is obtained from the calculated vales as ordinate and logarithms of the time constants (μsec), which are elapsed times after the stopping of the excitation light irradiation, as abscissa, and where the axis of ordinate and the axis of abscissa are taken as y-axis and x-axis, respectively, a value corresponding to an area surrounded by the elapse curve, the straight line of y=0 (x-axis), a straight line of $x=t_1$, and a straight line of $x=t_2$ ($t_1$ and $t_2$ are any time constants satisfying $t_1<t_2$) corresponds to a value which is proportional to a total defect density existing in the oxide semiconductor thin film. In other words, in the case where the axis of abscissas (x-axis) of the elapse curve is expressed as logarithm of time and the section of the curve ranging from $x=t_1$ to $x=t_2$ is integrated, the resultant integral is proportional to the total defect density existing in the oxide semiconductor thin film. A representative example of said area is the area surrounded by the elapse curve, the axis of ordinate (straight line of x=0), and the axis of abscissa (straight line of y=0). In the case where the elapse curve does not cross the axis of abscissa (straight line of y=0), the area surrounded by the elapse curve, the axis of ordinate (straight line of x=0), and a straight line of $x=t_3$ ($t_3$ is the time constant corresponding to the terminal (right-hand end) of the elapse curve) corresponds to said area.

It is known that the threshold voltage change $\Delta V_{th}$ between before and after light irradiation and negative-bias or positive-bias application to a thin film transistor, in the case of back channel etch type (BCE-) TFT which will be described later, is proportional to the total defect density which exists in the oxide semiconductor thin film and is causative of threshold shifts.

Consequently, the threshold voltage change $\Delta V_{th}$ between before and after light irradiation and negative-bias or positive-bias application to a thin film transistor can be evaluated on the basis of the integral (a value corresponding to the area surrounded by the elapse curve, the straight line of y=0, a straight line of $x=t_1$, and a straight line of $x=t_2$).

The step in which the energy level of the defect state existing in the oxide semiconductor thin film and the defect density are estimated from the peak value and the time constant, as explained in the first embodiment, can be conducted in combination with the step in which the total defect density existing in the oxide semiconductor thin film is estimated from the area surrounded by the elapse curve, the straight line of y=0, a straight line of $x=t_1$, and a straight line of $x=t_2$, as explained in the second embodiment. By conducting the first embodiment and the second embodiment in combination, the stress stability can be more accurately evaluated.

A method for evaluating an oxide semiconductor thin film according to the second embodiment of the present invention was described above.

The present invention includes a method in which the evaluation method is applied to any of steps for semiconductor production to control the quality of the oxide semiconductor thin film. The stress stability of the oxide semiconductor thin film is evaluated by applying the evaluation method to any of the production steps and the results of the evaluation are fed back or otherwise used to regulate the production conditions. Thus, the quality of the oxide semiconductor thin film can be appropriately controlled.

The wording "any of steps" means any step among semiconductor production steps. Investigations made by the present inventors revealed that production steps which may affect stress stability include (i) deposition step of a gate insulating film, (ii) deposition step of an oxide semiconductor thin film, (iii) heat treatment step after the deposition of the oxide semiconductor thin film (hereinafter often referred to as "pre-anneal step"), (iv) deposition step of a passivation film which may be formed on the surface of the oxide semiconductor thin film, and (v) heat treatment step after the deposition of the passivation film (hereinafter often referred to as "post-anneal treatment"). For example, by applying the evaluation method to these steps, the quality of the oxide semiconductor thin film can be controlled with satisfactory accuracy.

The passivation film, i.e., passivation insulating film, includes both an etch stopper layer for directly protecting the surface of the oxide semiconductor thin film and a final passivation film for further protecting the surface of this passivation film.

In the case of a BCE type transistor, for which electrodes are directly formed on a semiconductor layer and etching is then conducted to form channel parts, it is preferred to apply the evaluation method to steps such as (vi) BCE etching step and (vii) step of forming a passivation film after the etching.

Specifically, use may be made, for example, of a method in which an oxide semiconductor thin film is formed either after formation of a gate insulating film on a substrate or directly on a substrate without forming a gate insulating film and the evaluation method is conducted immediately thereafter. Alternatively, the evaluation method may be conducted after the oxide semiconductor thin film formed on a substrate or on a gate insulating film is subjected to a pre-anneal treatment with oxygen or water vapor, or before formation of a passivation film. Furthermore, the evaluation method may be conducted at one point in one of the production steps or may be conducted at multiple points in two or more steps. By applying the evaluation method of the invention to two or more steps as in the latter case, the in-plane distribution of threshold voltage in the oxide semiconductor thin film, i.e., in-plane unevenness in $V_{th}$, can be determined.

In the present invention, the evaluation method of the invention can be applied, for example, to the following: the case where an oxide semiconductor thin film is formed on a substrate; the case where a gate insulating film is formed and an oxide semiconductor thin film is then formed thereon; the case where an oxide semiconductor thin film is formed and a pre-anneal treatment is performed thereafter, wherein a gate insulating film may be formed before the formation of the oxide semiconductor thin film; the case where a passivation film is formed on the obtained oxide semiconductor thin film in any of these cases, wherein the passivation film may include a final passivation film for protecting said passivation film; or the case where a post-anneal treatment or the like is performed after any of these cases.

In the case where the evaluation method of the invention is used, the stress stability of oxide semiconductor thin films having various compositions and concentrations can be easily evaluated in a short time at low cost in developing materials for oxide semiconductor thin films. Furthermore, in cases when the evaluation method of the invention is used, the electrical properties of an oxide semiconductor thin film can be evaluated in a short time in a line for producing liquid-crystal display devises, etc. In addition, since the evaluation method can be carried out in a non-contact manner, improvements in production efficiency including an improvement in yield can be attained, and quality control of oxide semiconductors can be appropriately performed.

The present invention includes test elements to be evaluated by any of the evaluation methods described above. The test elements include a substrate and an oxide semiconductor thin film formed thereover, and have a configuration according to "any of steps" represented by the steps (i) to (vii) shown above, etc.

It is important that a test element which is suitable for examining the oxide semiconductor thin film for electronic state should be one in which the oxide semiconductor thin film has been directly formed on the surface of a substrate or gate insulating film. That is, no metal electrodes, e.g., gate electrodes, are present under the oxide semiconductor thin film. In the case where a gate electrode lies under the oxide semiconductor thin film, the gate electrode exerts a dominant influence on reflectance of the microwave because the gate electrode has free carriers in an amount as large as $10^{18}$ $cm^{-3}$ or more.

The test element is not particularly limited in configuration thereof, and may have a configuration according to the production step(s) into which the evaluation method of the invention is to be incorporated. Examples of the configuration of the test element include: (a) an element in which an oxide semiconductor thin film has been directly formed on the surface of a substrate; (b) an element in which an oxide semiconductor thin film has been directly formed on a gate insulating film formed on the surface of a substrate; and (c) an element in which a passivation film has been formed on the surface of the oxide semiconductor thin film of the (a) or (b) above. The passivation film may be an etch stopper layer or a final passivation film or may be both formed in this order.

The thin films laminated on the substrate, such as the oxide semiconductor thin film and the passivation film, may be ones which have been patterned according to need. For example, a gate insulating film, a patterned oxide semiconductor thin film, and an etch stopper layer which is a patterned passivation film may have been formed in this order over a substrate. A final passivation film may have been further formed thereon.

In the case of a BCE type transistor, for which electrodes are directly formed on a semiconductor layer and etching is then conducted to form channel parts, it is preferred to temporarily deposit a metal (e.g., molybdenum) serving as source/drain (S/D) electrodes, thereafter remove the metal by etching, and then subject the element to the examination. A passivation film may have been formed thereon.

The present invention further includes an evaluation device in which a plurality of test elements which are any of the test elements described above are arranged on a substrate.

Figure 8:
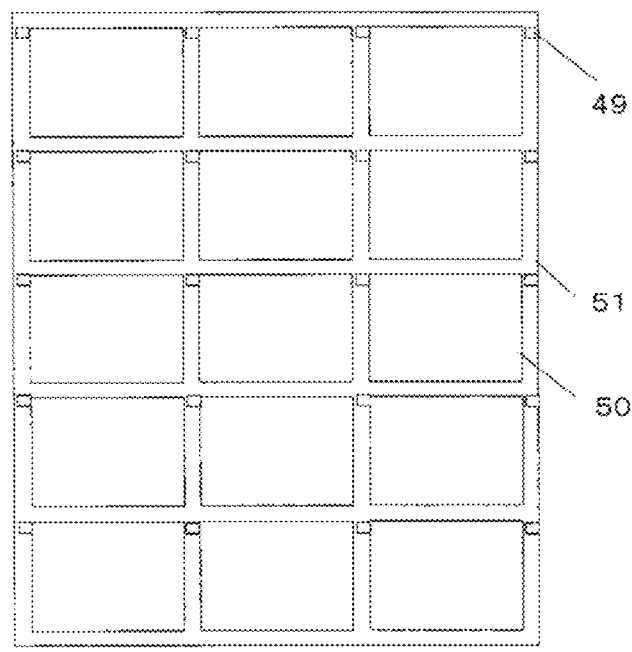
FIG. 8 is a diagrammatic view of a substrate for evaluation, the view showing an example of the arrangement of test elements to be evaluated in the present invention.

FIG. 8 is a diagrammatic view showing an example of the configuration of the test elements. As FIG. 8 shows, a plurality of test elements 49 have been regularly arranged and disposed on a mother glass 51 used in lines for mass-producing displays 50. Use of such evaluation device makes it possible to perform quality control of the oxide semiconductor thin film, specifically, to determine unevenness in threshold voltage $V_{th}$ within the plane of the substrate (hereinafter often referred to as "intra-substrate distribution") and unevenness in threshold voltage $V_{th}$ between substrates (hereinafter often referred to as "inter-substrate distribution").

[Quality Control Method]

The present invention includes a method for performing quality control of an oxide semiconductor thin film by applying the evaluation method described above. The quality control method may include applying the evaluation method of the invention in the manner described above and feeding back the results of the evaluation of the oxide semiconductor thin film for electronic state. By modifying the production conditions, specifically, the production conditions for at least one of the production steps (i) to (v) shown above, on the basis of the feedback, the defect in the oxide semiconductor thin film can be decreased. As a result, appropriate quality control of the oxide semiconductor thin film can be attained.

[Evaluation Device]

An embodiment of the present invention is explained below in detail by reference to a drawing. However, evaluation devices suitable for the present invention are not limited to ones having the following configuration, which can be suitably modified.

Figure 7:
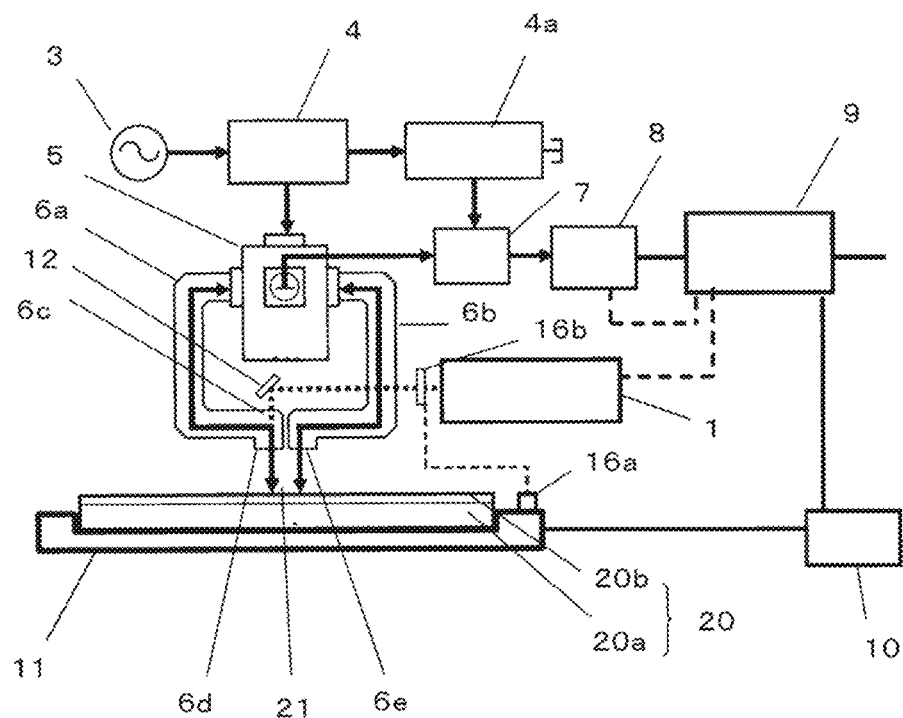
FIG. 7 is a diagrammatic view showing an example of evaluation devices usable in the present invention.

FIG. 7 is a diagrammatic view showing an example of the configuration of a device for use in examining an oxide semiconductor thin film using the μ-PCD technique in a non-contact manner. The evaluation device shown in FIG. 7 includes: an excitation light irradiation means 1 whereby an examination portion of a sample 20 having a configuration including a glass substrate 20a and an oxide semiconductor thin film 20b formed thereon is irradiated with excitation light to yield electron/hole pairs in the oxide semiconductor thin film; a microwave irradiation means 3 which irradiates the examination portion of the sample 20 with microwave; a reflected-microwave detection means 7 which determines the intensity of reflected microwave, which are the microwave reflected by the sample 20, the intensity being changed by the irradiation with the excitation light; and a means for evaluating the electrical resistivity of the sample 20 on the basis of detection data from the reflected-microwave detection means. Due to this configuration, changes in reflectance and the electrical resistivity can be determined or evaluated with the same device.

The excitation light irradiation means 1 preferably is one which has a light source that outputs energy not less than the bandgap of the oxide semiconductor thin film. For example, an ultraviolet laser may be used as the light source. Specific examples thereof include semiconductor lasers such as pulsed lasers which emit, as excitation light, pulsed ultraviolet light having a wavelength of 349 nm, a power of 1 μJ/pulse, a pulse duration of about 15 ns, and a beam diameter of about 1.5 mm. e.g., YLF laser third harmonic.

The excitation light irradiation means 1 emits pulsed light, as excitation light, upon input of a timing signal, as a trigger, sent (as indicated by broken lines in the figure) from the evaluation means 9. The timing signal is simultaneously transmitted also to a signal processor 8. The power of the excitation light emitted from the excitation light irradiation means 1 can be regulated with a power monitor for power regulation 16a and a power regulation means 16b.

The excitation light from the excitation light irradiation means 1 is reflected by an optical-path changing means 12 such as a mirror, is condensed by a light condensation means (not shown) such as a condenser lens, passes through a minute opening 6c formed in a first waveguide 6a, and is caused to strike on the examination portion having a diameter of, for example, about 5 to 10 μm of the sample 20 via an opening 6d of the first waveguide 6a which is close to the sample 20. Thus, excitation carriers generate in the excitation-light-irradiated region 21 in the sample 20.

Microwave emitted from the microwave irradiation means 3, e.g., a Gunn diode having a frequency of, for example, 26 GHz, are branched by a directional coupler 4, e.g., a 10-dB coupler. One of the branches of output microwave is transmitted to a magic T 5, and the other branch of output microwave is transmitted to a phase adjuster 4a and the LO input terminal of the reflected-microwave detection means 7.

The output microwave transmitted to the magic T 5 are branched into two; and one of the microwave branches is caused to strike on the excitation-light-irradiated region 21 of the sample 20 through the first waveguide (waveguide for signal) 6a, and the resultant reflected wave is transmitted to the magic T 5 through the first waveguide 6a again. The other branch of microwave is caused to strike on a region of the sample 20 other than the excitation-light-irradiated region 21 through a second waveguide 6b, which is a reference waveguide, and the resultant reflected wave is transmitted to the magic T 5 through the second waveguide 6b. From the magic T 5, a difference signal indicating the difference between these reflectance is transmitted to the RF input terminal of the reflected-microwave detection means 7.

The reflected-microwave detection means 7 mixes the microwave transmitted to the LO input terminal with the difference signal for the reflectance to thereby obtain a detection signal Sg1 and outputs the detection signal Sg1 to the signal processor 8. The detection signal Sg1 is a signal indicating an example of the intensity of a reflected-wave difference signal Rt1.

The intensity of the reflected-wave difference signal Rt1 detected by the reflected-microwave detection means 7 is changed by the irradiation of the examination portion of the sample 20 with excitation light. Specifically, the intensity of the reflected-wave difference signal Rt1 temporarily increases due to the irradiation with the excitation light and then declines. The larger the amount of impurities, defects, etc. in the examination portion, the smaller the peak value of the intensity of the reflected-wave difference signal Rt1 and the shorter the decay time, i.e., the carrier lifetime.

With respect to the intensity of the reflected-wave difference signal Rt1, which is changed by the irradiation with excitation light, the intensity thereof has a peak value and, after the stopping of the excitation-light irradiation, shows a slow decay. A parameter corresponding to the slow decay is an index to the electrical resistivity of the sample 20.

The signal processor 8 is a device which detects a peak value Sp of changes in the intensity of the reflected-wave difference signal Rt1 determined by the reflected-microwave detection means 7 and transmits the results of the detection to the evaluation means 9. More specifically, the signal processor 8, upon input of a timing signal as a trigger from the evaluation means 9, monitors changes of the reflected-wave difference signal Rt1 for a given time period and detects a highest-level value of reflected-wave difference signals Rt1 obtained during the period, as a peak value Sp of intensity changes of the reflected-wave difference signals Rt1. The signal processor 8 is equipped with a delay circuit for delaying reflected-wave difference signals Rt1, successively determines the intensities of the delayed signals at a given sampling frequency, and detects a peak value Sp of intensity changes of the reflected-wave difference signals Rt1 from the change in the determined intensity values.

As the evaluation means 9, use can be made of a computer including a CPU, a storage unit, an input/output signal interface, etc. The CPU performs a given program to thereby carry out various kinds of processing.

For example, the evaluation means 9 not only outputs a timing signal, which indicates the timing of emitting excitation light, to both the excitation light irradiation means 1 and the signal processor 8, but also inputs to itself the peak value Sp of reflected-wave difference signals Rt1 detected by the signal processor 8 and records the peak value Sp in the storage unit of the evaluation means 9. The recorded reflected-wave difference signals Rt1 (detected data) are used for evaluating the electrical resistivity of the sample 20.

A stage controller 10 controls an X-Y stage 11 in accordance with a command from the evaluation means 9, thereby controlling the positioning of the examination portion of the sample 20.

A sample table (not shown) has been disposed on the X-Y stage 11. The sample table is a platy conductor member made of a metal, such as aluminum, stainless steel, or iron, or another conductor. A substrate holding part (not shown) has been disposed on the sample table, and the sample 20 is placed on the substrate holding part.

The substrate holding part is a solid dielectric fixed to the upper surface of the sample table. The substrate holding part is a solid dielectric to be interposed between a substrate and the sample table, and the material thereof is, for example, a dielectric having a relatively high refractive index, such as glass or ceramic. Thus, the microwave transmitted by this substrate holding part as a medium have a shortened wavelength. A substrate holding part which is thinner and more lightweight can hence be employed.

According to the configuration of the present invention for evaluating electrical resistivity, photoexcitation carriers are yielded in the oxide semiconductor thin film by excitation light emitted from the excitation light irradiation means 1, and the photoexcitation carriers move due to an electrical field formed by microwave emitted from the microwave irradiation means 3. The movement is affected by the presence of impurities, defects, etc. in the semiconductor. Consequently, the intensity of the microwave reflected by the sample is determined by the reflected-microwave detection means 7, and changes in excess-carrier concentration are analyzed by the evaluation means 9 as explained above. Thus, the carrier concentration in the oxide semiconductor thin film can be determined and the electrical resistivity can be evaluated indirectly from a change in electronic state. In cases when the evaluation means 9 controls the position of the stage including the X-Y stage 11, etc. in this operation, it is possible to perform a mapping examination for determining the electrical resistivity of the oxide semiconductor thin film within a given region.

[Process for Producing Thin Film Transistor and Semiconductor Production Apparatus]

By applying the evaluation method to a process for TFT production, a TFT including an oxide semiconductor thin film having excellent stress stability can be produced. The evaluation method of the invention described above is widely applicable to various kinds of known semiconductor production apparatus. It is hence possible to estimate the energy level of defect and the defect density and to accurately and easily evaluate the stress stability.

A TFT includes a substrate, a gate insulating film, an oxide semiconductor thin film which have been formed over the substrate, a passivation film formed on the surface of the oxide semiconductor thin film, and source and drain electrodes. It is only required in producing the TFT that the oxide semiconductor thin film, the passivation film, or the like should be deposited under conditions determined on the basis of the evaluation of an oxide semiconductor thin film.

EXAMPLES

The present invention is explained below in more detail by reference to Examples, but the invention should not be construed as being limited by the following Examples. The present invention can of course be appropriately modified within a range conforming to the gist of the invention shown herein. All such modifications are included in the technical range of the present invention.

Example 1

Figure 9:
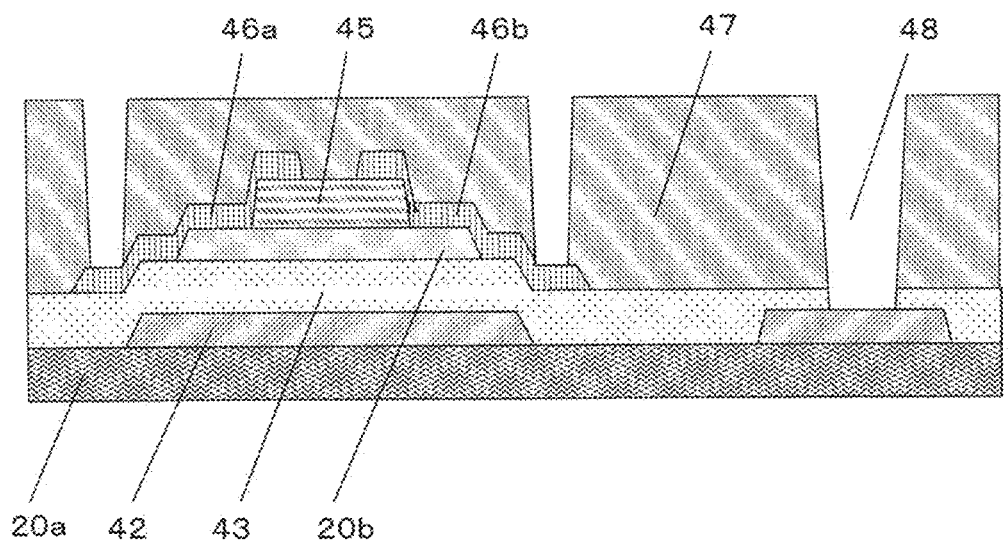
FIG. 9 diagrammatically shows an example of the cross-sectional structure of an ESL type TFT to be used in the present invention.

(1) Production of TFT Samples for Examining TFT Characteristics and Stress Stability Etch stopper layer (ESL) type TFTs shown in FIG. 9 were produced. First, on a glass substrate 20a having dimensions of 6 inches×thickness 0.7 mm were successively deposited an Mo thin film in a thickness of 100 nm as a gate electrode 42 and an $SiO_2$ gate insulating film 43 in a thickness of 200 nm. The gate electrode 42 was formed by DC sputtering using pure Mo as a sputtering target. The sputtering conditions included a substrate temperature of room temperature and a gas pressure of 2 mTorr. The gate insulating film 43 was formed using plasma CVD under the condition of carrier gas: mixed gas composed of $SiH_4$ and $N_2O$, $N_2O$=100 sccm, $SiH_4$=4 sccm, and $N_2$=36 sccm, deposition power: 300 W, and deposition temperature: 320° C.

Next, IGZO was deposited as an oxide semiconductor thin film 20b by sputtering. In this Example, the oxygen addition amount was changed as shown below to produce a plurality of samples.

Sputtering apparatus: "CS-200" manufactured by ULVAC, Inc.
Composition of sputtering target: $InGaZnO_4$ [In:Ga:Zn=1:1:1 (atomic ratio)]
Substrate temperature: room temperature
Thickness of oxide semiconductor thin film: 40 nm
Gas pressure: 1 mTorr
Oxygen addition amounts:
$O_2/(Ar+O_2)$=4% (by volume); Samples 2-1, 2-2
12% (by volume); Samples 2-3, 2-4
20% (by volume); Samples 2-5, 2-6

After the oxide semiconductor thin film 20b had been thus formed, patterning was conducted by photolithography and wet etching. As a wet etchant was used "ITO-07N", manufactured by Kanto Chemical Co., Ltd.

After the oxide semiconductor thin film 20b had been thus patterned, a pre-anneal treatment was conducted in order to improve the film quality.

The pre-anneal treatment was conducted at 350° C. in the air at atmospheric pressure for 1 hour.

Next, an etch stopper layer was formed as a passivation film 45 on the oxide semiconductor thin film 20b. In this Example, the carrier gas to be used in forming the passivation film 45 was changed as shown below to produce a plurality of samples.

Gas pressure: 133 Pa
Deposition power: 100 W
Deposition temperature: 230° C.
Film thickness: 100 nm
Feed gas:
$N_2O$=100 sccm, $SiH_4/N_2$=4/36 sccm;
Samples 2-1, 2-3, 2-5
$N_2O$=150 sccm, $SiH_4/N_2$=6/54 sccm:
Samples 2-2, 2-4, 2-6

After the passivation film 45 had been thus formed, patterning was conducted by photolithography and wet etching. As a wet etchant was used "ITO-07N", manufactured by Kanto Chemical Co., Ltd.

Next, pure Mo was used to deposit a film in a thickness of 100 nm by DC sputtering, and patterning was thereafter conducted to form a source electrode 46a and a drain electrode 46b. The deposition of the pure Mo film and the patterning were conducted by the same methods as for the gate electrode described above, and the TFT channel length and channel width were regulated to 10 μm and 200 μm, respectively.

Furthermore, a multilayer film composed of an $SiO_2$ film having a thickness of 200 nm and an SiN film having a thickness of 200 nm was formed as a final passivation film 47. The final passivation film 47 was formed by plasma CVD using "PD-220NL", manufactured by Samco Inc. In this Example, a plasma treatment with $N_2O$ gas was performed, and $SiO_2$ and SiN were thereafter successively formed under the following conditions. A mixed gas composed of $SiH_4$, $N_2$, and $N_2O$ was used for forming the $SiO_2$, and a mixed gas composed of $SiH_4$, $N_2$, and $NH_3$ was used for forming the SiN. In either case, the deposition power was 100 W and the deposition temperature was 150° C. These conditions for the protective layer were common to all the samples.

(First Layer): $SiO_2$
  Carrier gas: $SiH_4/N_2$=4/36 sccm: $N_2O$=100 sccm
  Gas pressure: 133 Pa
  Deposition power: 100 W
  Deposition temperature: 150° C.

(Second Layer): SiN
  Carrier gas: $SiH_4$=12.5 sccm; $N_2$=297.5 sccm: $NH_3$=6 sccm
  Gas pressure: 133 Pa
  Deposition power: 100 W
  Deposition temperature: 150° C.

Next, a contact hole 48 for a probe for transistor characteristics evaluation was formed in the final passivation film 47 by photolithography and dry etching, thereby obtaining an ESL type TFT.

After the formation of the contact hole 48, a heat treatment was conducted as final anneal at 250° C. for 30 minutes in the air at atmospheric pressure. Thus, TFT Samples Nos. 1-1 to 1-6 for stress stability examination were produced.

[Evaluation of Stress Stability]

Each TFT sample was examined for threshold shift $\Delta V_{th}$. In this Example, a stress environment encountered in actual panel driving was simulated to conduct a stress application test in which the sample was irradiated with light while applying a negative bias to the gate electrode. The stress application conditions were as follows. The wavelength of the light was regulated to about 400 nm, which was close to the bandgap of the oxide semiconductor and was apt to result in fluctuations in transistor characteristics.

Stress stability Evaluation Conditions
  Gate voltage: −20 V
  Substrate temperature: 60° C.
  Photo-induced stress
    Light source: white-light source
    Intensity of light to strike on TFT, in illuminance: 25,000 NIT
    Illuminator: YSM-1410, manufactured by Yang Electronics Co.
    Stress application period: 2 hours (2) Production of Test Elements Test Elements Nos. 2-1 to 2-6 for lifetime examination were produced under the same conditions as for the TFTs produced in (1) above, except that the gate electrode 42 was not disposed. The thus-produced test elements were used to acquire decay waveforms by the g-PCD technique under the following measuring conditions. The structures of Test Elements Nos. 2-1 to 2-6 were respectively the same as those of TFT Samples Nos. 1-1 to 1-6 except for the gate electrode.

[Measuring Conditions in μ-PCD Technique]
  Laser wavelength: 349 nm (ultraviolet light)
  Laser energy: 10 μJ
  Pulse duration: 5 ns
  Beam diameter: 1.5 mmφ
  Pulse number in one examination: 16,384 shots
  Apparatus: LTA-1610SP(K) (manufactured by Kobelco Research Institute, Inc.)

[Arithmetic Processing]

The test element was irradiated with excitation light and microwave to determine a maximum value of reflectance of the microwave by the test element. Subsequently, the irradiation with the excitation light was stopped and the temporal reflectance of the microwave by the test element were measured with the lapse of time after the stopping of the excitation light irradiation, and the reflectance of the microwave for each of elapsed times (μsec) after the stopping of the excitation light irradiation was recorded as a signal value. Each of the signal values for the respective elapsed times was substituted into Equation (1) [x=(signal value)×(elapsed time for the signal value); in the equation, x is the calculated value, the signal value (mV) is the reflectance of the microwave, and the elapsed time for the signal value is the time (μsec) which had elapsed from the stopping of the excitation light irradiation to the signal value]. The calculated values thus obtained (relative values) were plotted as ordinate and the time constants were plotted as abscissa, thereby obtaining a graph. The results obtained are shown in FIG. 2.

In a Reference Example, values of $t_2$ were calculated from microwave reflectance decay curves drawn by plotting those signal values, in accordance with the procedure described in Patent Document 1. Specifically, the slope of a segment obtained from a reflected-wave intensity decay curve ranging from $1/e$ to $1/e^2$ the maximum value of the reflected-microwave intensity by subjecting the decay curve to conversion into logarithm was calculated as $\tau_2$. The samples are referred to as Samples Nos. 3-1 to 3-6.

Figure 3:
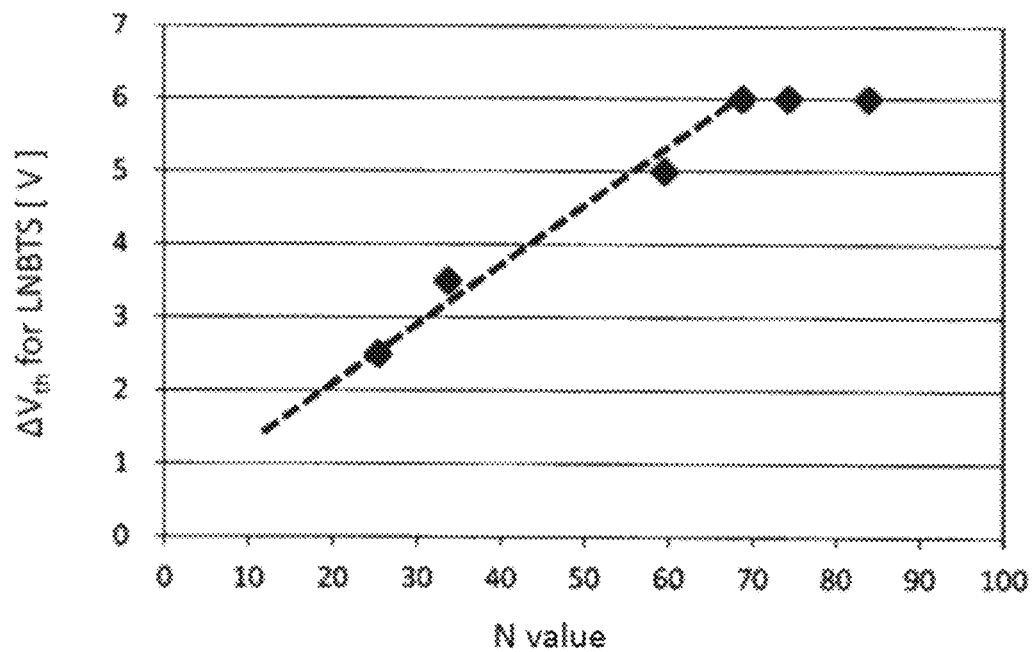
FIG. 3 is a graph showing a relationship between: peak values obtained in Example 1 by subjecting reflected-microwave decay waveforms obtained by the μ-PCD technique to the arithmetic processing according to the present invention; and threshold voltage changes $\Delta V_{th}$ obtained by an LNBTS test.

FIG. 2 is graphs obtained by plotting the results obtained by subjecting reflected-microwave decay waveforms obtained by the μ-PCD technique to the arithmetic processing according to the present invention. As FIG. 2 shows, each test element showed such a waveform that the calculated value reached a highest peak value (N value) at an abscissa of about 10 to 20 μsec and the calculated value increased at a constant slope toward the N value and thereafter declined. Meanwhile, N values according to the present invention and the values of threshold shift $\Delta V_{th}$ obtained in the LNBTS test, which had been obtained by examining Samples Nos. 2-1 to 2-6, were plotted as abscissa axis and ordinate, respectively, and the results of the plotting are shown in FIG. 3. As FIG. 3 shows, the larger the N value, the larger the threshold shift $\Delta V_{th}$.

Figure 4:
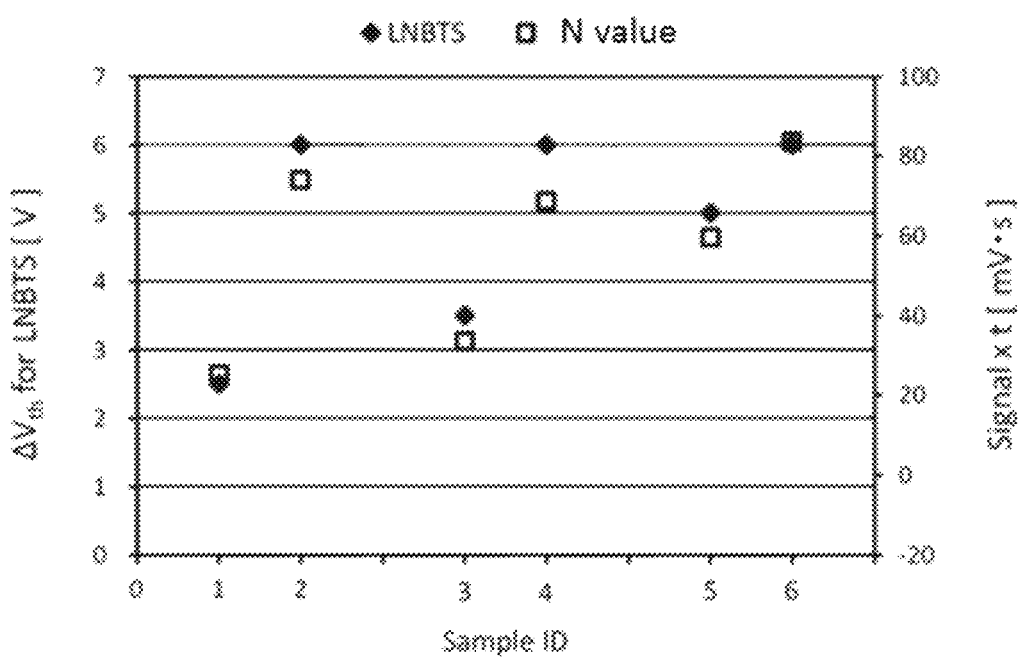
FIG. 4 is a presentation showing a correlation between the LNBTS test and the evaluation method of the present invention.

FIG. 4 shows a relationship between the N value, which was obtained from the results of arithmetic processing of results of an examination made by the μ-PCD technique, and the threshold shift $\Delta V_{th}$ determined by the LNBTS test. As FIG. 4 shows, the N value approximately coincided with the threshold voltage change $\Delta V_{th}$ determined by the LNBTS test, and a strong correlation was observed therebetween. In FIG. 4, Sample IDs. 1 to 6 respectively are combinations of Samples Nos. 1-1 to 1-6 with Test Elements Nos. 2-1 to 2-6, which had corresponding structures. For example, Sample ID. 1 is a combination of Sample No. 1-1 with Test Element No. 2-1. Likewise, Sample IDs. 1 to 6 in FIG. 5 respectively are combinations of Samples Nos. 1-1 to 1-6 with Samples Nos. 3-1 to 3-6.

FIG. 5 shows a relationship between the slope $t_2$ of slow decay acquired from decay waveforms by the μ-PCD technique and the threshold shift $\Delta V_{th}$ determined by the LNBTS test. As FIG. 5 shows, the values of $t_2$ are separated from the values of threshold shift $\Delta V_{th}$ determined by the LNBTS test. The calculated value (N value) according to the present invention has a higher correlation with the threshold shift $\Delta V_{th}$ than the slow-decay slope $\tau_2$, as shown in FIG. 4.

Figure 6:
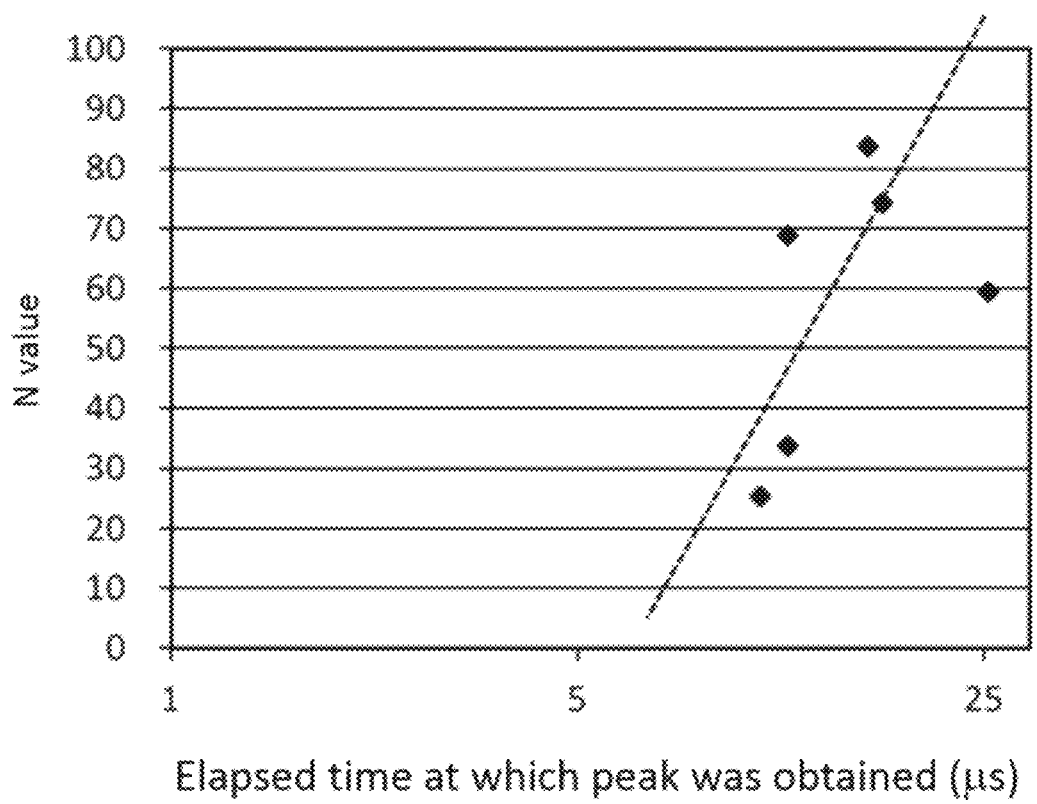
FIG. 6 is a presentation showing a relationship obtained in Example 1 between the N values of samples and the elapsed times at which the peaks were obtained.

FIG. 6 shows a plot indicating a relationship between the N values of the samples shown in FIG. 2 and the elapsed times at which the peaks were obtained. There is a relationship wherein the longer the time which had elapsed to the point of time when the peak was obtained, the larger the N value. This relationship is approximately a proportional correlation.

Consequently, on the basis of the calculated values obtained by substituting the results of an examination by the μ-PCD technique into Equation (1), the energy level of defect existing in the bandgap of the oxide semiconductor thin film and the defect density can be estimated from N values and from the elapsed times at which the peaks were obtained. Furthermore, the method according to the present invention can more accurately estimate the stress stability than the conventional method in which the μ-PCD technique is used.

Example 2

Figure 10:
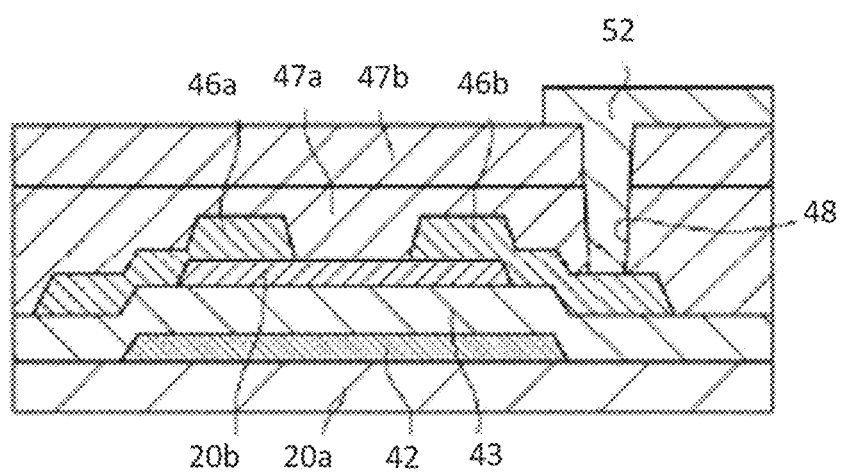
FIG. 10 diagrammatically shows an example of the cross-sectional structure of a BCE type TFT to be used in the present invention.

(1) Production of TFT Samples for Examining TFT Characteristics and Stress Stability Back channel etch (BCE) type thin film transistors having the structure shown in FIG. 10 were produced.

First, on a glass substrate 20a (Eagle XG, manufactured by Corning Glass Works; diameter 100 nm×thickness 0.7 mm) were successively deposited a pure Mo thin film in a thickness of 100 nm as a gate electrode 42 and an $SiO_x$ film (thickness, 250 nm) as a gate insulating film 43. The gate electrode 42 was deposited by DC sputtering using a pure-Mo sputtering target under the conditions of deposition temperature: room temperature, deposition power: 300 W, carrier gas: Ar, and a gas pressure: 2 mTorr. The gate insulating film 43 was deposited using plasma CVD under the conditions of carrier gas: $SiH_4/N_2O$ mixed gas, deposition power: 300 W, and deposition temperature: 350° C.

Next, IGZO was deposited as an oxide semiconductor thin film 20b (thickness, 40 nm) by sputtering. The sputtering target had the composition $InGaZnO_4$ [In:Ga:Zn=1:1:1 (atomic ratio)]. The apparatus used for the sputtering was "CS-200", manufactured by ULVAC, Inc., and the sputtering conditions were as follows.

[Sputtering Conditions]
Substrate temperature: room temperature
Deposition power: DC 200 W
Gas pressure: 1 mTorr
Partial pressure of oxygen: $100 \times O_2/(Ar+O_2) = 4\%$ After the oxide semiconductor thin film 20b had been thus deposited, patterning was conducted by photolithography and wet etching. In the wet etching, "ITO-07N", manufactured by Kanto Chemical Co., Ltd., was used and the liquid temperature was room temperature. In this Example, it was ascertained that all the oxide thin films used in the experiments had been able to be etched without leaving a residue.

After the oxide semiconductor thin film 20b had been thus patterned, a pre-anneal treatment was conducted in order to improve the film quality of the oxide semiconductor thin film 20b. The pre-anneal treatment was conducted at 350° C. in the air for 60 minutes.

Next, a source electrode 46a and a drain electrode 46b were formed. Specifically, a thin film (thickness, 100 nm) of an Mo—Ti alloy (1:1 by mole) was formed. After the deposition of the source electrode 46a and the drain electrode 46b, patterning was conducted by photolithography and wet etching. For the patterning was used an inorganic etchant including an aqueous solution of hydrogen peroxide as a main component. By the patterning of the source electrode 46a and the drain electrode 46b, the TFT channel length and channel width were regulated to 10 μm and 200 μm, respectively. In order to prevent the source electrode 46a and drain electrode 46b from short-circuiting, 60-second over-etching was conducted.

Thereafter, first, as a final passivation film, an $SiO_x$ film as a first passivation film 47a was formed. The $SiO_x$ film was formed by plasma CVD using "PD-220NL", manufactured by Samco Inc. An $SiH_4/N_2O$ mixed gas was used for forming the $SiO_x$ film. The deposition power was 100 W and the deposition temperature was 230° C. The $SiH_4/N_2O$ gas ratio was $SiH_4:N_2O=4:100$, and the $SiO_x$ film thus formed had a hydrogen concentration of 4.3 atom %. The $SiO_x$ film had a thickness of 200 nm.

After the formation of the $SiO_x$ film as a passivation film, a silicone resin was applied in a thickness of 600 nm with a spin coater (rotational speed, 1,000 rpm). After the application, a pre-baking treatment was conducted at 90° C. for 2 minutes, followed by exposure with an exposure device, baking at 90° C. for 60 seconds with a hot plate, and then development. After the development, post-baking was conducted at 180° C. for 60 minutes in a nitrogen atmosphere.

Thereafter, an $SiN_x$ film was deposited as a second passivation film 47b. The $SiN_x$ film was formed by plasma CVD using "PD-220NL", manufactured by Samco Inc., like the first passivation film 47a. An $SiH_4/NH_3/N_2$ mixed gas was used for forming the $SiN_x$ film. The deposition power was 100 W and the deposition temperature was 200° C. The $SiH_4/NH_3/N_2$ gas ratio was $SiH_4:NH_3:N_2=12.5:6.0:297.5$.

Next, a contact hole 48 for a probe for transistor characteristics evaluation was formed in the first passivation film 47a and second passivation film 47b by photolithography and dry etching. A transparent electroconductive film 52 was electrically connected to the drain electrode 46b via the contact hole 48.

Finally, a post-anneal treatment was conducted. The post-anneal treatment was conducted for 30 minutes in a nitrogen atmosphere. The post-anneal temperature was set at three levels of 250° C., 270° C., and 300° C. Thus, BCE type TFTs were obtained.

[Examination of Transistor Characteristics]

The TFTs of Example 2 were measured for $I_d$-$V_g$ characteristics. The gate voltage and the source/drain electrode voltages were set as shown below to examine the $I_d$-$V_g$ characteristics using a prober and a semiconductor parameter analyzer (Keithley 4200SCS).
Gate voltage: −30 to 30 V (step, 0.25 V)
Source voltage: 0 V
Drain voltage: 10 V
Measuring temperature: room temperature

[Evaluation of Stress Stability]

Figure 11A:
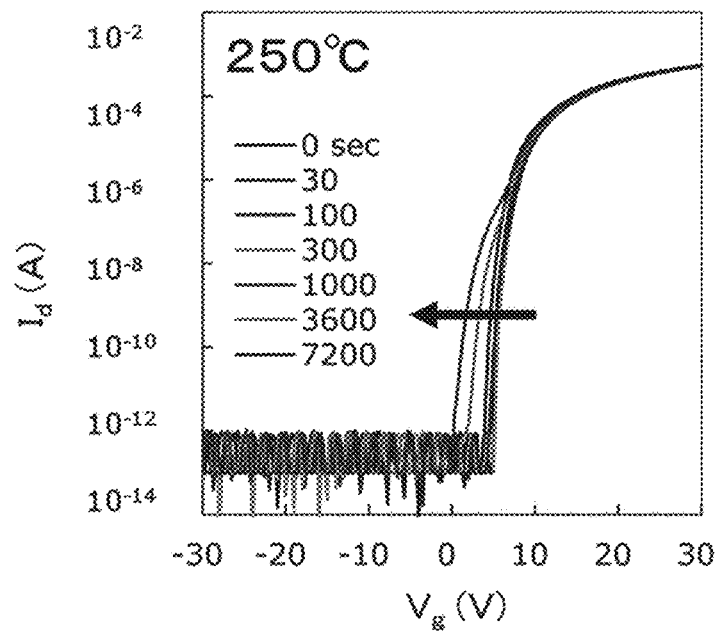
FIG. 11A shows an example of data obtained by an LNBTS test of a BCE type TFT (post anneal temperature, 250° C.) to be used in the present invention.
Figure 11B:
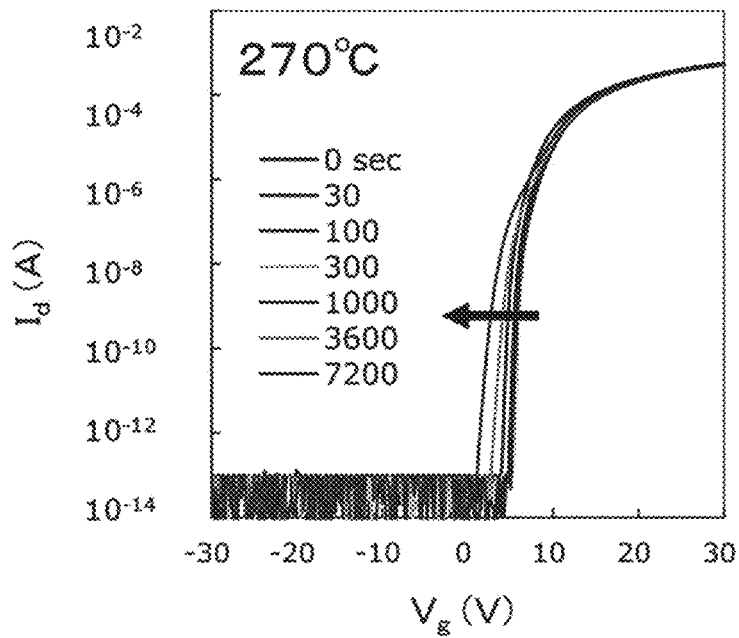
FIG. 11B shows an example of data obtained by an LNBTS test of a BCE type TFT (post anneal temperature, 270° C.) to be used in the present invention.
Figure 11C:
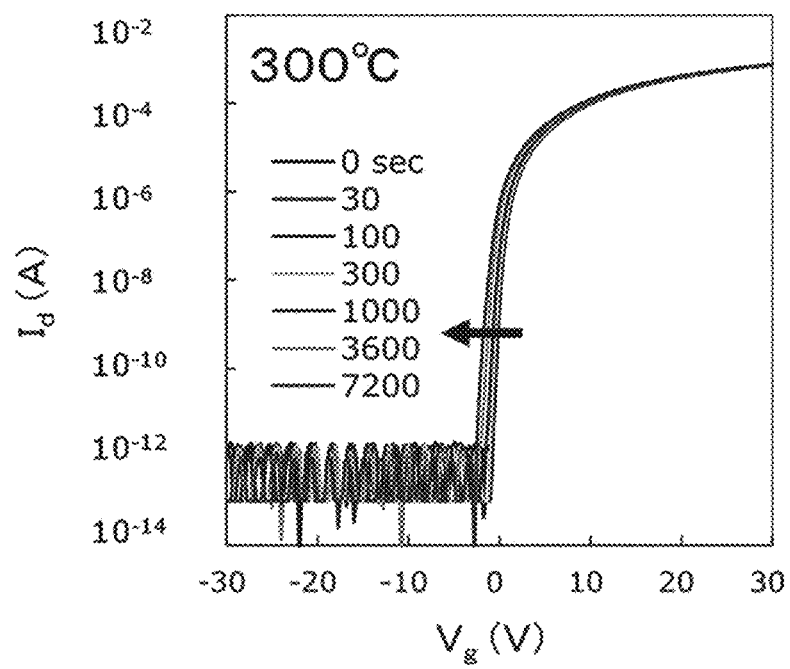
FIG. 11C shows an example of data obtained by an LNBTS test of a BCE type TFT (post anneal temperature, 300° C.) to be used in the present invention.

The TFTs of Example 2 were evaluated for stress stability (resistance to photo-induced stress and negative-bias stress). As in Example 1, the stress stability was evaluated by performing a stress application test in which each TFT was irradiated with light while applying a negative bias to the gate electrode. The stress imposition conditions were as follows.
Gate voltage: −20 V
Source/drain voltage: 10 V
Substrate temperature: 60° C.
Stress imposition period: 2 hours
Photo-induced stress conditions:
Light intensity: 25,000 NIT
Light source: white LED Subsequently, the TFT was measured for threshold voltage shift (change in the gate voltage at which the drain current was $10^{-9}$ A) through the application of photo-induced stress and negative-bias stress. This change is called $\Delta V_{th}$. The results ($I_d$-$V_g$ characteristics) of this LNBTS test are shown in FIG. 11A to FIG. 11C. FIG. 11A shows the case where the post-anneal temperature was 250° C., FIG. 11B shows the case where the post-anneal temperature was 270° C., and FIG. 11C shows the case where the post-anneal temperature was 300° C. In each figure, the $I_d$-$V_g$ curves correspond to different stress application periods (0 sec, 30 sec, 100 sec, 300 sec, 1,000 sec, 3,600 sec, and 7,200 sec).

It can be seen from each of FIG. 11A to FIG. 11C that the longer the stress application period, the larger the threshold voltage shift (the more the TFT characteristics graph shifts from right to left as indicated by the arrow in the figure). Furthermore, as apparent from FIG. 11A to FIG. 11C, a minimum value of threshold voltage shift $\Delta V_{th}$ was obtained in the TFT for which the post-anneal temperature had been 300° C.

(2) Production of Test Elements

Test elements for lifetime examination were produced under the same conditions as for the TFTs produced above, except that the gate electrode 42 was not disposed. The thus-produced test elements were used to acquire decay waveforms by the μ-PCD technique under the same conditions as in Example 1. In producing the test elements, a post-anneal treatment was conducted for 30 minutes in a nitrogen atmosphere at three levels of post-anneal temperature of 250° C., 270° C., and 300° C., as in the case of producing the TFTs.

[Arithmetic Processing]

Figure 12A:
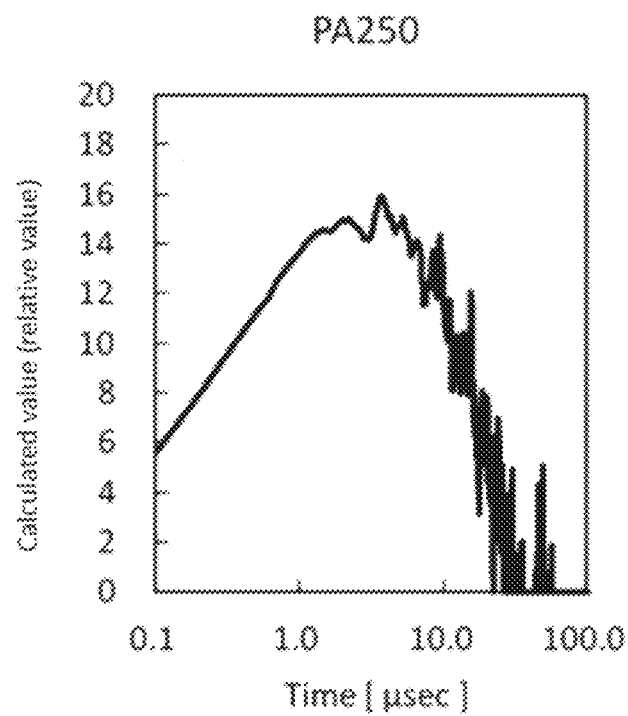
FIG. 12A is a graph showing the results obtained in Example 2 (BCE type TFT; post anneal temperature, 250° C.) by subjecting reflected-microwave decay waveforms obtained by the μ-PCD technique to the arithmetic processing according to the present invention.
Figure 12B:
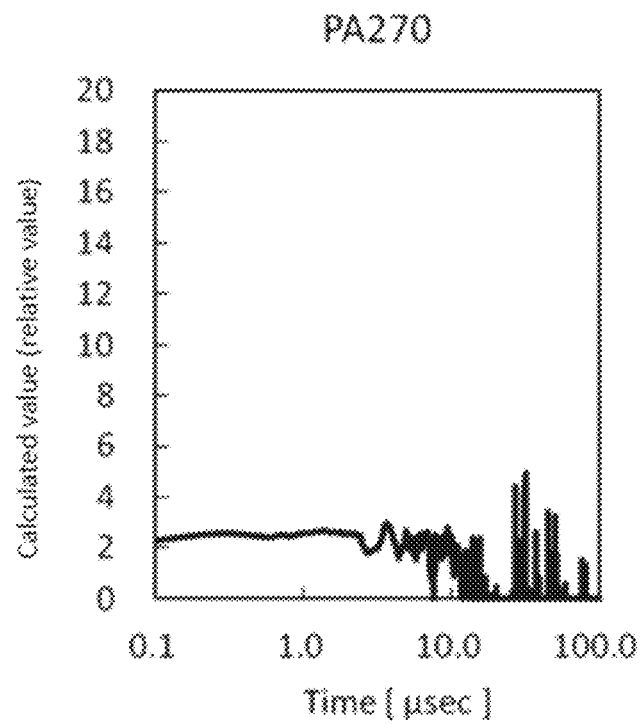
FIG. 12B is a graph showing the results obtained in Example 2 (BCE type TFT; post anneal temperature, 270° C.) by subjecting reflected-microwave decay waveforms obtained by the μ-PCD technique to the arithmetic processing according to the present invention.
Figure 12C:
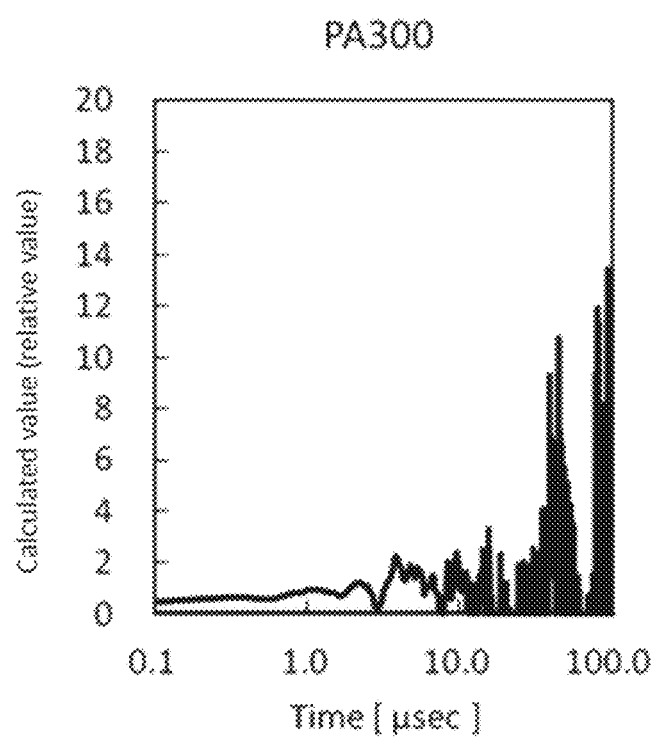
FIG. 12C is a graph showing the results obtained in Example 2 (BCE type TFT; post anneal temperature, 300° C.) by subjecting reflected-microwave decay waveforms obtained by the μ-PCD technique to the arithmetic processing according to the present invention.

The three kinds of test elements differing in post-anneal temperature were each measured in the following manner as in Example 1. Each test element was irradiated with excitation light and microwave to determine a maximum value of reflectance of the microwave from the test element. Subsequently, the irradiation with the excitation light was stopped and the temporal reflectance of the microwave from the test element were measured with the lapse of time after the stopping of the excitation light irradiation, and the reflectance of the microwave for each of elapsed times (μsec) after the stopping of the excitation light irradiation was recorded as a signal value. Each of the signal values for the respective elapsed times was substituted into Equation (1) [x=(signal value)×(elapsed time for the signal value); in the equation, x is the calculated value, the signal value (mV) is the reflectance of the microwave, and the elapsed time for the signal value is the time (μsec) which had elapsed from the stopping of the excitation light irradiation to the signal value]. The calculated values thus obtained were plotted as ordinate and the logarithms of the time constant (μsec), which were elapsed that had after the stopping of the excitation light irradiation, were plotted as abscissa. FIG. 12A to FIG. 12C show the results obtained by subjecting reflected-microwave decay waveforms obtained by the μ-PCD technique to the arithmetic processing according to the present invention. FIG. 12A shows the case where the post-anneal temperature was 250° C., FIG. 12B shows the case where the post-anneal temperature was 270° C. and FIG. 12C shows the case where the post-anneal temperature was 300° C.

With respect to each of the elapse curves obtained from those graphs by arithmetic processing, a value corresponding to the area surrounded by the elapse curve, the axis of ordinates (x=0), and the axis of abscissas (y=0) was calculated. Specifically, the logarithmic difference between adjoining measuring times was plotted as abscissa and the areas were added up in accordance with the trapezoidal formula (the region surrounded by the elapse curve, the axis of ordinates, and the axis of abscissas was integrated). Thus, the value of the area was calculated for each of the three kinds of test elements.

Figure 13:
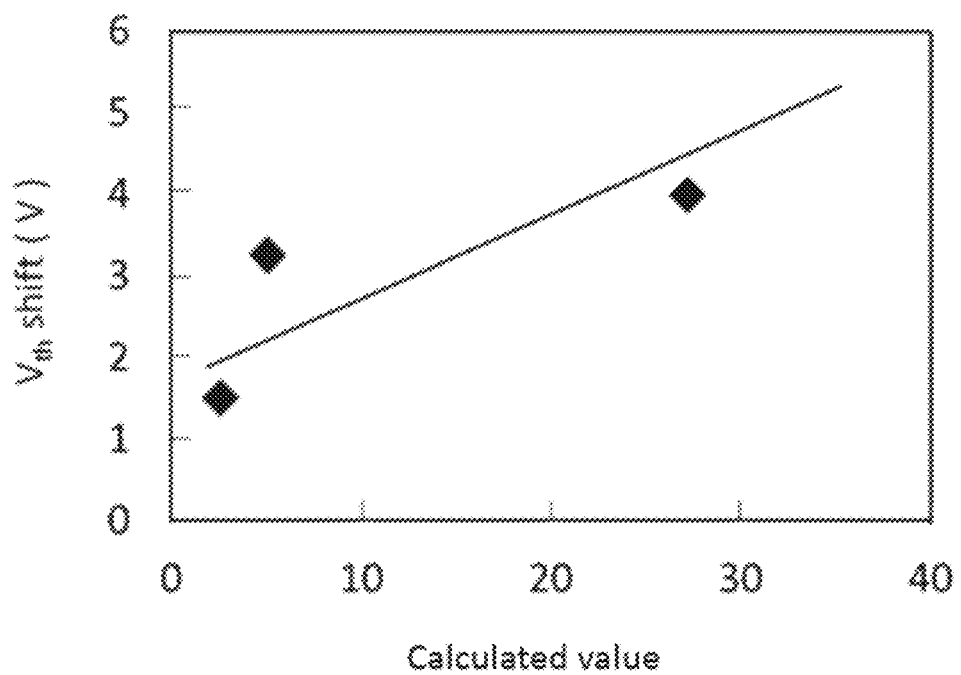
FIG. 13 is a graph showing a relationship between: peak values obtained in Example 2 by subjecting reflected-microwave decay waveforms obtained by the μ-PCD technique to the arithmetic processing according to the present invention; and threshold voltage changes $\Delta V_{th}$ obtained by an LNBTS test.

FIG. 13 is a graph obtained by plotting which shows a relationship between the calculated value (the value of area) obtained by performing the arithmetic processing in this Example and the threshold voltage change $\Delta V_{th}$ obtained by the LNBTS test. As FIG. 13 shows, the smaller the value of area (calculated value on the axis of abscissas), the smaller the value of threshold shift $\Delta V_{th}$ ($V_{th}$ shift on the axis of ordinates) in the stress test.

Example 3

Various kinds of BCE type thin film transistors having the same structure as in Example 2 (see FIG. 10) were produced in the same manner as in Example 2, except for the various production conditions shown in Table 1, which will be given later. Furthermore, test elements for lifetime examination were also produced under the same conditions as for those TFTs, except that the gate electrode 42 was not disposed. As shown in Table 1, in producing Samples Nos. 6 to 9, the oxygen concentration (partial oxygen pressure) during the sputtering for depositing IGZO as the oxide semiconductor thin film 20b was regulated to 20%. With respect to Samples Nos. 4 to 9, a heat treatment in the air was conducted at 300° C. for 1 hour as recovery anneal (recovery heat treatment) after an $SiO_x$ film had been formed as the first passivation film 47a. The post-anneal treatment conditions were set at four levels in total, which were post-anneal temperatures of 250° C., 270° C., and 300° C. and omission of the post-anneal treatment.

TABLE 1

| Sample No. | Oxide semiconductor film | Oxygen concentration during sputtering (%) | Recovery anneal (recovery heat treatment) | Post-anneal treatment |
| --- | --- | --- | --- | --- |
| 1 | IGZO | 4 | not performed | not performed |
| 2 | IGZO | 4 | not performed | 250° C. |
| 3 | IGZO | 4 | not performed | 300° C. |
| 4 | IGZO | 4 | performed | 270° C. |
| 5 | IGZO | 4 | performed | 300° C. |
| 6 | IGZO | 20 | performed | not performed |
| 7 | IGZO | 20 | performed | 250° C. |
| 8 | IGZO | 20 | performed | 270° C. |
| 9 | IGZO | 20 | performed | 300° C. |

Figure 14A:
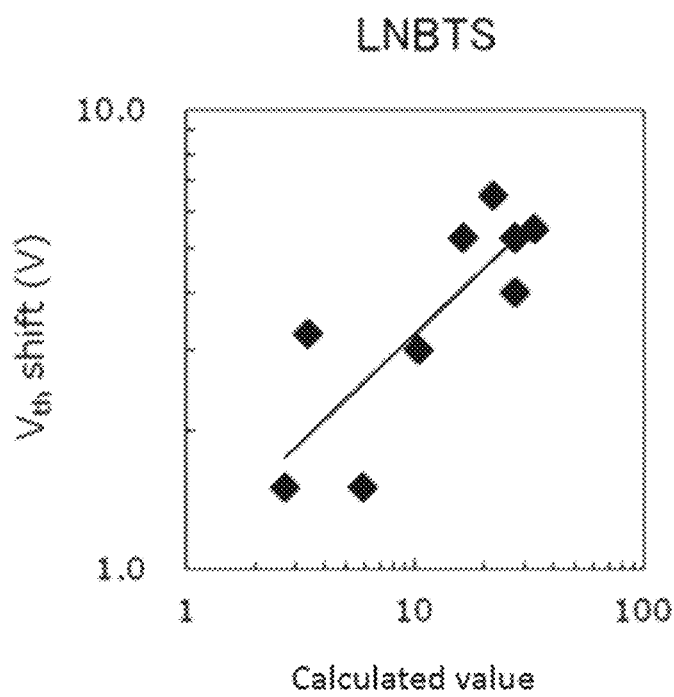
FIG. 14A is a graph showing a relationship between: peak values obtained in Example 3 by subjecting reflected-microwave decay waveforms obtained by the μ-PCD technique to the arithmetic processing according to the present invention; and threshold voltage changes $\Delta V_{th}$ obtained by an LNBTS test.

FIG. 14A is a graph obtained by plotting, which shows a relationship between the calculated value (the value of area) obtained by performing the arithmetic processing according to this Example under the same conditions as those shown in Example 2 and the threshold voltage change $\Delta V_{th}$ obtained by the LNBTS test. As FIG. 14A shows, the smaller the value of area (calculated value on the axis of abscissas in the graph), the smaller the threshold shift $\Delta V_{th}$ ($V_{th}$ shift on the axis of ordinates in the graph) in the stress test, as in the case of the LNBTS test (Example 2) shown in FIG. 13.

Furthermore, the TFTs of Example 3 were each subjected to evaluation of stress stability, i.e., resistance to positive-bias stress (PBTS test). The stress application conditions in the PBTS test were as follows.

Gate voltage: +20 V
Source/drain voltage: 0 V

Figure 14B:
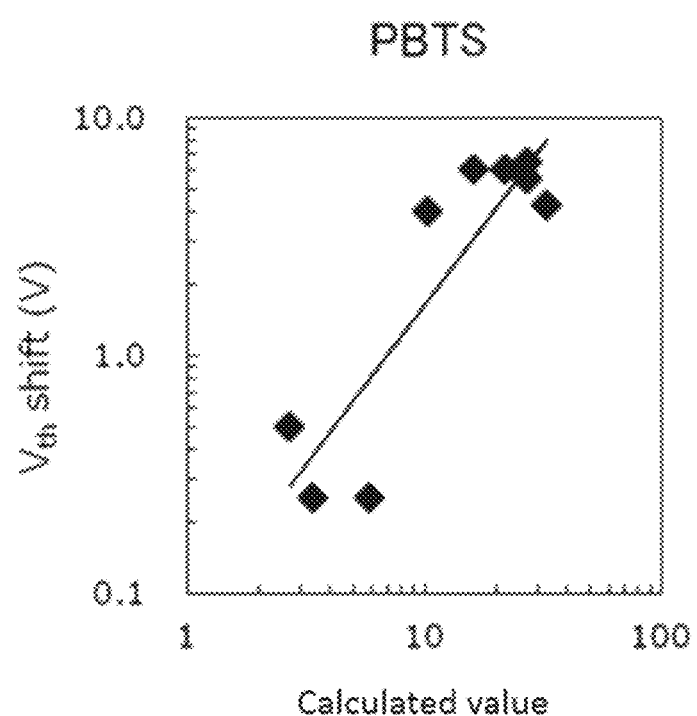
FIG. 14B is a graph showing a relationship between: peak values obtained in Example 3 by subjecting reflected-microwave decay waveforms obtained by the μ-PCD technique to the arithmetic processing according to the present invention; and threshold voltage changes $\Delta V_{th}$ obtained by a PBTS test.

Substrate temperature: 60° C.
Stress imposition period: 2 hours
Photo-induced stress conditions: none FIG. 14B is a graph obtained by plotting, which shows a relationship between the calculated value (the value of area) obtained by performing the arithmetic processing according to this Example under the same conditions as those shown in Example 2 and the threshold voltage change $\Delta V_{th}$ obtained by the PBTS test. As FIG. 14B shows, the smaller the value of area (calculated value on the axis of abscissas in the graph), the smaller the threshold shift $\Delta V_{th}$ ($V_{th}$ shift on the axis of ordinates in the graph) in this PBTS test, as in the case of the LNBTS test shown in FIG. 13 and FIG. 14A.

Consequently, the total defect density existing in the bandgap of an oxide semiconductor thin film can be estimated from the results of an examination made by the μ-PCD technique, on the basis of a calculated value of the area surrounded by the elapse curve, the straight line of y=0, a straight line of x=$t_1$, and a straight line of x=$t_2$ ($t_1$ and $t_2$ are any time constants satisfying $t_1 < t_2$). In addition, the stress stability can be more accurately estimated than by the conventional method employing μ-PCD technique.

As described above, an oxide semiconductor thin film is measured and evaluated for electronic state, and production conditions including conditions for depositing the oxide semiconductor thin film and conditions for depositing a passivation film are regulated on the basis of the evaluation to optimize the electronic state of the oxide semiconductor thin film. Thus, an oxide semiconductor thin film reduced in defects can be formed and a TFT having satisfactory stress stability can be produced.

While the invention has been described in detail and with reference to specific embodiments thereof, it will be apparent to one skilled in the art that various changes and modifications can be made therein without departing from the spirit and scope thereof. This application is based on a Japanese patent application No. 2016-088984 filed on Apr. 27, 2016, a Japanese patent application No. 2017-054971 filed on Mar. 21, 2017, and a Japanese patent application No. 2017-086647 filed on Apr. 25, 2017, the entire contents thereof being incorporated herein by reference.

DESCRIPTION OF THE REFERENCE NUMERALS AND SIGNS

1 Excitation light irradiation means
3 Microwave irradiation means
4 Directional coupler
4a Phase adjuster
5 Magic T
6a First waveguide
6b Second waveguide
6d, 6e Opening
6c Minute opening
7 Reflected-microwave detection means
8 Signal processor
9 Evaluation means
10 Stage controller
11 X-Y stage
12 Optical-path changing means
16a Power monitor for power regulation
16b Power regulation means
20 Sample
20a Glass substrate
20b Oxide semiconductor thin film
21 Excitation-light-irradiated region
42 Gate electrode
43 Gate insulating film
45 Etch stopper layer or passivation film
46a Source electrode
46b Drain electrode
47 Final passivation film
47a First passivation film
47b Second passivation film
48 Contact hole
49 Test element
50 Display
51 Mother glass
52 Transparent electroconductive film

The invention claimed is:

1. A quality evaluation method for an oxide semiconductor thin film comprising:
a first step, which comprises; irradiating a sample having an oxide semiconductor thin film formed thereover with excitation light and microwave to measure a maximum value of reflectance of the microwave from the oxide semiconductor thin film; subsequently stopping the irradiation with the excitation light; measuring temporal reflectance of the microwave from the oxide semiconductor thin film with the lapse of time after the stopping of the excitation light irradiation; and recording the reflectance of the microwave as a signal value for each of elapsed times (μsec) after the stopping of the excitation light irradiation; and
a second step, which comprises; selecting a peak value having a largest calculated value and a time constant (μsec) for the peak value among calculated values obtained by substituting each signal value for respective elapsed times after stopping the excitation light irradiation and the corresponding elapsed time into the following Equation (1); and estimating, from the peak value and the time constant, an energy level of defect state and the defect density existing in the oxide semiconductor thin film:

$$x = (\text{signal value}) \times (\text{elapsed time for the signal value}) \quad \text{Equation 1,}$$

wherein
x: calculated value,
signal value (mV): reflectance of the microwave, and
elapsed time for the signal value: time (μsec) which has elapsed from the stopping of the excitation light irradiation to the signal value.

2. The quality evaluation method for an oxide semiconductor thin film according to claim 1, wherein in the second step, the peak value having a largest calculated value and the time constant (μsec) for the peak value are selected on the basis of a microwave-reflectance elapse curve obtained from the calculated values as ordinate and the time constants (μsec) as abscissa.

3. The quality evaluation method for an oxide semiconductor thin film according to claim 1, wherein, on the basis of the peak value and the time constant for the peak value, light irradiation and negative-bias or positive-bias are applied to a thin film transistor to evaluate threshold voltage change $\Delta V_{th}$ between before and after the application.

4. The quality evaluation method for an oxide semiconductor thin film according to claim 1, wherein in the second step, in the case where a microwave reflectance elapse curve is obtained from the calculated vales as ordinate and logarithms of the time constants (μsec), which are elapsed times after the stopping of the excitation light irradiation, as abscissa, and where the axis of the ordinate and the axis of the abscissa are taken as y-axis and x-axis respectively, a total defect density existing in the oxide semiconductor thin film is estimated from a value of an area surrounded by the elapse curve, the straight line of y=0, a straight line of $x=t_1$, and a straight line of $x=t_2$, wherein $t_1$ and $t_2$ are any time constants satisfying $t_1<t_2$.

5. The quality evaluation method for an oxide semiconductor thin film according to claim 4, wherein, on the basis of the value of the area surrounded by the elapse curve, the straight line of y=0, the straight line of $x=t_1$, and the straight line of $x=t_2$, light irradiation and negative-bias or positive-bias are applied to a thin film transistor to evaluate threshold voltage change $\Delta V_{th}$ between before and after the application.

6. The quality evaluation method for an oxide semiconductor thin film according to claim 1, wherein the oxide semiconductor thin film comprises at least one element selected from the group consisting of In, Ga, Zn, and Sn.

7. The quality evaluation method for an oxide semiconductor thin film according to claim 1, wherein the oxide semiconductor thin film is deposited on a surface of a gate insulating film.

8. The quality evaluation method for an oxide semiconductor thin film according to claim 1, wherein the oxide semiconductor thin film has a passivation film on a surface thereof.

9. A method for controlling the quality of an oxide semiconductor thin film, wherein the evaluation method according to claim 1 is applied to at least one of the steps for manufacturing a semiconductor.

* * * * *